United States Patent [19]

Ikeyama et al.

[11] Patent Number: 5,439,886
[45] Date of Patent: Aug. 8, 1995

[54] MONOCLONAL ANTIBODY, POLYPEPTIDES AND PRODUCTION THEREOF

[75] Inventors: Shuichi Ikeyama, Takatsuki; Masaru Koyama, Suita; Masayuki Miyake, Kyoto; Masaharu Senoo, Okayama, all of Japan

[73] Assignee: Takeda Chemical Industries, Ltd., Osaka, Japan

[21] Appl. No.: 254,493

[22] Filed: Jun. 6, 1994

Related U.S. Application Data

[63] Continuation of Ser. No. 865,552, Apr. 9, 1992, abandoned.

[30] Foreign Application Priority Data

Apr. 12, 1991 [JP] Japan .................. 3-079996
Apr. 17, 1991 [JP] Japan .................. 3-085396
Feb. 7, 1992 [JP] Japan .................. 4-022321

[51] Int. Cl.⁶ .............. A61K 39/00; C07K 2/00; C07K 4/00; C07H 19/00
[52] U.S. Cl. .................. 514/12; 435/7.2; 435/7.21; 435/7.23; 435/240.2; 435/240.23; 514/2; 530/350; 536/22.1; 536/23.1; 536/23.5
[58] Field of Search ............ 435/7.2, 7.21, 7.23, 435/240.2, 240.23; 514/2, 12; 530/350, 300; 536/22.1, 23.1, 23.5

[56] References Cited

FOREIGN PATENT DOCUMENTS 127173 5/1984 European Pat. Off. .

OTHER PUBLICATIONS

Yamada, et al. *Cancer Research*, 50(15):4485–4496 (1990).
Lanza, et al. *Journal of Biological Chemistry*, 266(16):10638–10645 (1991).
Miyake, et al., *Journal of Experimental Medicine*, 174(6:1347–1354 (1991).
Perlstein et al., "Effects of Antiplatelet antibody . . .", Cancer Research 44, 3884–3887 Sep. 1984.
M. Miyake et al., "A Specific Cel Surface Glcoconjugate Controlling Cell Motility" *Biochemistry*, 30, (1991), pp. 3328–3334.
C. Boucheix et al., "Molecular Cloning of the CD9 Antigen" *J. Biol. Chem.* (1991) pp. 117–122.

Primary Examiner—Keith C. Furman
Assistant Examiner—Hyosuk Kim
Attorney, Agent, or Firm—David G. Conlin; David S. Resnick

[57] ABSTRACT

The present invention relates to a monclonal antibody capable of suppressing the motility of cancer cells, a polypeptide recognizable by said anti-cancer antibody and its fragment peptides which is capable of suppressing the motility of cancer cells.

The present invention also relates to a production and a use for preventing the matastasis of cancer thereof.

3 Claims, 8 Drawing Sheets

```
GACCAGCCTA CAGCCGCCTG CATCTGTATC CAGCGCCAGG TCCTGCCAGT CCCAGCTGCG        60

CGCGCCCCCC AGTCCCGCAC CCGTTCGGCC CAGGCTAAGT TAGCCCTCAC C ATG CCG       117
                                                          Met Pro
                                                           -1   1

GTC AAA GGA GGC ACC AAG TGC ATC AAA TAC CTG CTG TTC GGA TTT AAC        165
Val Lys Gly Gly Thr Lys Cys Ile Lys Tyr Leu Leu Phe Gly Phe Asn
             5               10                  15

TTC ATC TTC TGG CTT GCC GGG ATT GCT GTC CTT GCC ATT GGA CTA TGG        213
Phe Ile Phe Trp Leu Ala Gly Ile Ala Val Leu Ala Ile Gly Leu Trp
             20              25                  30

CTC CGA TTC GAC TCT CAG ACC AAG AGC ATC TTC GAG CAA GAA ACT AAT        261
Leu Arg Phe Asp Ser Gln Thr Lys Ser Ile Phe Glu Gln Glu Thr Asn
         35              40                  45

AAT AAT AAT TCC AGC TTC TAC ACA GGA GTC TAT ATT CTG ATC GGA GCC        309
Asn Asn Asn Ser Ser Phe Tyr Thr Gly Val Tyr Ile Leu Ile Gly Ala
 50              55                  60                  65

GGC GCC CTC ATG ATG CTG GTG GGC TTC CTG GGC TGC TGC GGG GCT GTG        357
Gly Ala Leu Met Met Leu Val Gly Phe Leu Gly Cys Cys Gly Ala Val
             70                  75                  80

CAG GAG TCC CAG TGC ATG CTG GGA CTG TTC TTC GGC TTC CTC TTG GTG        405
Gln Glu Ser Gln Cys Met Leu Gly Leu Phe Phe Gly Phe Leu Leu Val
             85                  90                  95

ATA TTC GCC ATT GAA ATA GCT GCG GCC ATC TGG GGA TAT TCC CAC AAG        453
Ile Phe Ala Ile Glu Ile Ala Ala Ala Ile Trp Gly Tyr Ser His Lys
             100                 105                 110

GAT GAG TGT ATT AAG GAA GTC CAG GAG TTT TAC AAG GAC ACC TAC AAC        501
Asp Glu Cys Ile Lys Glu Val Gln Glu Phe Tyr Lys Asp Thr Tyr Asn
 115                 120                 125

AAG CTG AAA ACC AAG GAT GAG CCC CAG CGG GAA ACG CTG AAA GCC ATC        549
Lys Leu Lys Thr Lys Asp Glu Pro Gln Arg Glu Thr Leu Lys Ala Ile
 130             135                 140                 145
```

FIG. 4A

```
CAC TAT GCG TTG AAC TGC TGT GGT TTG GCT GGG GGC GTG GAA CAG TTT       597
His Tyr Ala Leu Asn Cys Cys Gly Leu Ala Gly Gly Val Glu Gln Phe
            150             155             160

ATC TCA GAC ATC TGC CCC AAG AAG GAC GTA CTC GAA ACC TTC ACC GTG       645
Ile Ser Asp Ile Cys Pro Lys Lys Asp Val Leu Glu Thr Phe Thr Val
            165             170             175

AAG TCC TGT CCT GAT GCC ATC AAA GAG GTC TTC GAC AAT AAA TTC CAC       693
Lys Ser Cys Pro Asp Ala Ile Lys Glu Val Phe Asp Asn Lys Phe His
            180             185             190

ATC ATC GGC GCA GTG GGC ATC GGC ATT GCC GTG GTC ATG ATA TTT GGC       741
Ile Ile Gly Ala Val Gly Ile Gly Ile Ala Val Val Met Ile Phe Gly
    195             200             205

ATG ATC TTC AGT ATG ATC TTG TGC TGT GCT ATC CGC AGG AAC CGC GAG       789
Met Ile Phe Ser Met Ile Leu Cys Cys Ala Ile Arg Arg Asn Arg Glu
210             215             220             225

ATG GTC TAGAGTCAGC TTACATCCCT GAGCAGGAAA GTTTACCCAT GAAGATTGGT        845
Met Val

GGGATTTTTT GTTTGTTTGT TTTGTTTTGT TTGTTGTTTG TTGTTTGTTT TTTTGCCACT     905

AATTTTAGTA TTCATTCTGC ATTGCTAGAT AAAAGCTGAA GTTACTTTAT GTTTGTCTTT     965

TAATGCTTCA TTCAATATTG ACATTTGTAG TTGAGCGGGG GGTTTGGTTT GCTTTGGTTT    1025

ATATTTTTTC AGTTGTTTGT TTTTGCTTGT TATATTAAGC AGAAATCCTG CAATGAAAGG    1085

TACTATATTT GCTAGACTCT AGACAAGATA TTGTA                               1120
```

FIG. 4B

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 227 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

|  | Pro<br>1 | Val | Lys | Gly<br>5 | Gly | Thr | Lys | Cys | Ile<br>10 | Lys | Tyr | Leu | Leu | Phe<br>15 | Gly | Phe |
|---|---|---|---|---|---|---|---|---|---|---|---|---|---|---|---|---|
|  | Asn | Phe | Ile | Phe<br>20 | Trp | Leu | Ala | Gly | Ile<br>25 | Ala | Val | Leu | Ala | Ile<br>30 | Gly | Leu |
|  | Trp | Leu | Arg<br>35 | Phe | Asp | Ser | Gln | Thr<br>40 | Lys | Ser | Ile | Phe | Glu<br>45 | Gln | Glu | Thr |
|  | Asn | Asn<br>50 | Asn | Asn | Ser | Ser | Phe<br>55 | Tyr | Thr | Gly | Val | Tyr<br>60 | Ile | Leu | Ile | Gly |
|  | Ala<br>65 | Gly | Ala | Leu | Met | Met<br>70 | Leu | Val | Gly | Phe | Leu<br>75 | Gly | Cys | Cys | Gly | Ala<br>80 |
|  | Val | Gln | Glu | Ser | Gln<br>85 | Cys | Met | Leu | Gly | Leu<br>90 | Phe | Phe | Gly | Phe | Leu<br>95 | Leu |
|  | Val | Ile | Phe | Ala<br>100 | Ile | Glu | Ile | Ala | Ala<br>105 | Ala | Ile | Trp | Gly | Tyr<br>110 | Ser | His |
|  | Lys | Asp | Glu<br>115 | Val | Ile | Lys | Glu | Val<br>120 | Gln | Glu | Phe | Tyr | Lys<br>125 | Asp | Thr | Tyr |
|  | Asn | Lys<br>130 | Leu | Lys | Thr | Lys | Asp<br>135 | Glu | Pro | Gln | Arg | Glu<br>140 | Thr | Leu | Lys | Ala |
|  | Ile<br>145 | His | Tyr | Ala | Leu | Asn<br>150 | Cys | Cys | Gly | Leu | Ala<br>155 | Gly | Gly | Val | Glu | Gln<br>160 |
|  | Phe | Ile | Ser | Asp | Ile<br>165 | Cys | Pro | Lys | Lys | Asp<br>170 | Val | Leu | Glu | Thr | Phe<br>175 | Thr |
|  | Val | Lys | Ser | Cys<br>180 | Pro | Asp | Ala | Ile | Lys<br>185 | Glu | Val | Phe | Asp | Asn<br>190 | Lys | Phe |
|  | His | Ile | Ile<br>195 | Gly | Ala | Val | Gly | Ile<br>200 | Gly | Ile | Ala | Val | Val<br>205 | Met | Ile | Phe |
|  | Gly | Met<br>210 | Ile | Phe | Ser | Met | Ile<br>215 | Leu | Cys | Cys | Ala | Ile<br>220 | Arg | Arg | Asn | Arg |
|  | Glu<br>225 | Met | Val |  |  |  |  |  |  |  |  |  |  |  |  |  |

(2) INFORMATION FOR SEQ ID NO:2:

(i) SEQUENCE CHARACTERISTICS:
        (A) LENGTH: 687 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL: NO (iv) ANTI-SENSE: NO (vi) ORIGINAL SOURCE:
        (A) ORGANISM: HUMAN
        (G) CELL TYPE: BREAST CARCINOMA
        (H) CELL LINE: ZR-75-1

(xi) SEQUENCE DESCRIPTION: SEQ ID NO:2:

```
ATGCCGGTCA AAGGAGGCAC CAAGTGCATC AAATACCTGC TGTTCGGATT TAACTTCATC      60

TTCTGGCTTG CCGGGATTGC TGTCCTTGCC ATTGGACTAT GGCTCCGATT CGACTCTCAG     120

ACCAAGAGCA TCTTCGAGCA AGAAACTAAT AATAATAATT CCAGCTTCTA CACAGGAGTC     180

TATATTCTGA TCGGAGCCGG CGCCCTCATG ATGCTGGTGG GCTTCCTGGG CTGCTGCGGG     240

GCTGTGCAGG AGTCCCAGTG CATGCTGGGA CTGTTCTTCG GCTTCCTCTT GGTGATATTC     300

GCCATTGAAA TAGCTGCGGC CATCTGGGGA TATTCCCACA AGGATGAGGT GATTAAGGAA     360

GTCCAGGAGT TTTACAAGGA CACCTACAAC AAGCTGAAAA CCAAGGATGA GCCCCAGCGG     420

GAAACGCTGA AAGCCATCCA CTATGCGTTG AACTGCTGTG GTTTGGCTGG GGGCGTGGAA     480
```

```
CAGTTTATCT CAGACATCTG CCCCAAGAAG GACGTACTCG AAACCTTCAC CGTGAAGTCC     540

TGTCCTGATG CCATCAAAGA GGTCTTCGAC AATAAATTCC ACATCATCGG CGCAGTGGGC     600

ATCGGCATTG CCGTGGTCAT GATATTTGGC ATGATCTTCA GTATGATCTT GTGCTGTGCT     660

ATCCGCAGGA ACCGCGAGAT GGTCTAG                                          687
```

( 2 ) INFORMATION FOR SEQ ID NO:3:

( i ) SEQUENCE CHARACTERISTICS:
        ( A ) LENGTH: 1120 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
        ( A ) ORGANISM: HUMAN
        ( G ) CELL TYPE: BREAST CARCINOMA
        ( H ) CELL LINE: ZR-75-1

( i x ) FEATURE:
        ( A ) NAME/KEY: CDS
        ( B ) LOCATION: 112..795

( i x ) FEATURE:
        ( A ) NAME/KEY: mat peptide
        ( B ) LOCATION: 115..795

( x i ) SEQUENCE DESCRIPTION: SEQ ID NO:3:

```
GACCAGCCTA CAGCCGCCTG CATCTGTATC CAGCGCCAGG TCCTGCCAGT CCCAGCTGCG      60

CGCGCCCCCC AGTCCCGCAC CCGTTCGGCC CAGGCTAAGT TAGCCCTCAC C ATG CCG      117
                                                          Met Pro
                                                          - 1   1

GTC AAA GGA GGC ACC AAG TGC ATC AAA TAC CTG CTG TTC GGA TTT AAC       165
Val Lys Gly Gly Thr Lys Cys Ile Lys Tyr Leu Leu Phe Gly Phe Asn
          5                  10                  15

TTC ATC TTC TGG CTT GCC GGG ATT GCT GTC CTT GCC ATT GGA CTA TGG       213
Phe Ile Phe Trp Leu Ala Gly Ile Ala Val Leu Ala Ile Gly Leu Trp
        20                  25                  30

CTC CGA TTC GAC TCT CAG ACC AAG AGC ATC TTC GAG CAA GAA ACT AAT       261
Leu Arg Phe Asp Ser Gln Thr Lys Ser Ile Phe Glu Gln Glu Thr Asn
    35                  40                  45

AAT AAT AAT TCC AGC TTC TAC ACA GGA GTC TAT ATT CTG ATC GGA GCC       309
Asn Asn Asn Ser Ser Phe Tyr Thr Gly Val Tyr Ile Leu Ile Gly Ala
50              55                  60                  65

GGC GCC CTC ATG ATG CTG GTG GGC TTC CTG GGC TGC TGC GGG GCT GTG       357
Gly Ala Leu Met Met Leu Val Gly Phe Leu Gly Cys Cys Gly Ala Val
                70                  75                  80

CAG GAG TCC CAG TGC ATG CTG GGA CTG TTC TTC GGC TTC CTC TTG GTG       405
Gln Glu Ser Gln Cys Met Leu Gly Leu Phe Phe Gly Phe Leu Leu Val
            85                  90                  95

ATA TTC GCC ATT GAA ATA GCT GCG GCC ATC TGG GGA TAT TCC CAC AAG       453
Ile Phe Ala Ile Glu Ile Ala Ala Ala Ile Trp Gly Tyr Ser His Lys
        100                 105                 110

GAT GAG TGT ATT AAG GAA GTC CAG GAG TTT TAC AAG GAC ACC TAC AAC       501
Asp Glu Cys Ile Lys Glu Val Gln Glu Phe Tyr Lys Asp Thr Tyr Asn
    115                 120                 125

AAG CTG AAA ACC AAG GAT GAG CCC CAG CGG GAA ACG CTG AAA GCC ATC       549
Lys Leu Lys Thr Lys Asp Glu Pro Gln Arg Glu Thr Leu Lys Ala Ile
130                 135                 140                 145

CAC TAT GCG TTG AAC TGC TGT GGT TTG GCT GGG GGC GTG GAA CAG TTT       597
```

|     |     |     |     |     |     |     |     |     |     |     |     |     |     |     |     |
| --- | --- | --- | --- | --- | --- | --- | --- | --- | --- | --- | --- | --- | --- | --- | --- |
| His | Tyr | Ala | Leu | Asn | Cys | Cys | Gly | Leu | Ala | Gly | Gly | Val | Glu | Gln | Phe |
|     |     |     |     | 150 |     |     |     |     | 155 |     |     |     |     | 160 |     |

| ATC | TCA | GAC | ATC | TGC | CCC | AAG | AAG | GAC | GTA | CTC | GAA | ACC | TTC | ACC | GTG | 645 |
| --- | --- | --- | --- | --- | --- | --- | --- | --- | --- | --- | --- | --- | --- | --- | --- | --- |
| Ile | Ser | Asp | Ile | Cys | Pro | Lys | Lys | Asp | Val | Leu | Glu | Thr | Phe | Thr | Val |     |
|     |     |     | 165 |     |     |     |     | 170 |     |     |     |     | 175 |     |     |     |

| AAG | TCC | TGT | CCT | GAT | GCC | ATC | AAA | GAG | GTC | TTC | GAC | AAT | AAA | TTC | CAC | 693 |
| --- | --- | --- | --- | --- | --- | --- | --- | --- | --- | --- | --- | --- | --- | --- | --- | --- |
| Lys | Ser | Cys | Pro | Asp | Ala | Ile | Lys | Glu | Val | Phe | Asp | Asn | Lys | Phe | His |     |
|     |     | 180 |     |     |     |     | 185 |     |     |     |     | 190 |     |     |     |     |

| ATC | ATC | GGC | GCA | GTG | GGC | ATC | GGC | ATT | GCC | GTG | GTC | ATG | ATA | TTT | GGC | 741 |
| --- | --- | --- | --- | --- | --- | --- | --- | --- | --- | --- | --- | --- | --- | --- | --- | --- |
| Ile | Ile | Gly | Ala | Val | Gly | Ile | Gly | Ile | Ala | Val | Val | Met | Ile | Phe | Gly |     |
|     | 195 |     |     |     |     | 200 |     |     |     |     | 205 |     |     |     |     |     |

| ATG | ATC | TTC | AGT | ATG | ATC | TTG | TGC | TGT | GCT | ATC | CGC | AGG | AAC | CGC | GAG | 789 |
| --- | --- | --- | --- | --- | --- | --- | --- | --- | --- | --- | --- | --- | --- | --- | --- | --- |
| Met | Ile | Phe | Ser | Met | Ile | Leu | Cys | Cys | Ala | Ile | Arg | Arg | Asn | Arg | Glu |     |
| 210 |     |     |     |     | 215 |     |     |     |     | 220 |     |     |     |     | 225 |     |

| ATG | GTC | TAGAGTCAGC | TTACATCCCT | GAGCAGGAAA | GTTTACCCAT | GAAGATTGGT | 845 |
| --- | --- | --- | --- | --- | --- | --- | --- |
| Met | Val |     |     |     |     |     |     |

| GGGATTTTTT | GTTTGTTTGT | TTTGTTTTGT | TTGTTGTTTG | TTGTTTGTTT | TTTTGCCACT | 905 |
| --- | --- | --- | --- | --- | --- | --- |

| AATTTTAGTA | TTCATTCTGC | ATTGCTAGAT | AAAAGCTGAA | GTTACTTTAT | GTTTGTCTTT | 965 |
| --- | --- | --- | --- | --- | --- | --- |

| TAATGCTTCA | TTCAATATTG | ACATTGTAG | TTGAGCGGGG | GGTTTGGTTT | GCTTTGGTTT | 1025 |
| --- | --- | --- | --- | --- | --- | --- |

| ATATTTTTC | AGTTGTTTGT | TTTGCTTGT | TATATTAAGC | AGAAATCCTG | CAATGAAAGG | 1085 |
| --- | --- | --- | --- | --- | --- | --- |

| TACTATATTT | GCTAGACTCT | AGACAAGATA | TTGTA | 1120 |
| --- | --- | --- | --- | --- |

( 2 ) INFORMATION FOR SEQ ID NO:4:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

| Lys | Asp | Glu | Val | Ile | Lys | Glu | Val | Gln | Glu | Phe | Tyr | Lys | Asp | Thr | Tyr |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |

| Asn | Lys | Leu | Lys | Thr | Lys | Asp | Glu | Pro | Gln | Arg | Glu | Thr | Leu |
| --- | --- | --- | --- | --- | --- | --- | --- | --- | --- | --- | --- | --- | --- |
|     |     |     | 20 |     |     |     |     | 25 |     |     |     |     | 30 |

( 2 ) INFORMATION FOR SEQ ID NO:5:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| Gln | Arg | Glu | Thr | Leu | Lys | Ala | Ile | His | Tyr | Ala | Leu | Asn | Cys | Cys | Gly |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |

| Leu | Ala | Gly | Gly | Val | Glu | Gln | Phe | Ile | Ser | Asp | Ile | Cys |
| --- | --- | --- | --- | --- | --- | --- | --- | --- | --- | --- | --- | --- |
|     |     |     | 20 |     |     |     |     | 25 |     |     |     |     |

( 2 ) INFORMATION FOR SEQ ID NO:6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Ser Asp Ile Cys Pro Lys Lys Asp Val Leu Glu Thr Phe Thr Val Lys
 1               5                   10                      15

Ser Cys Pro Asp Ala Ile Lys Glu Val Phe Asp Asn Lys
             20                  25
```

( 2 ) INFORMATION FOR SEQ ID NO:7:

( i ) SEQUENCE CHARACTERISTICS:
      ( A ) LENGTH: 26 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:7:

```
Arg Phe Asp Ser Gln Thr Lys Ser Ile Phe Glu Gln Glu Thr Asn Asn
 1               5                   10                      15

Asn Asn Ser Ser Phe Tyr Thr Gly Val Tyr
             20                  25
```

MONOCLONAL ANTIBODY, POLYPEPTIDES AND PRODUCTION THEREOF

This is a continuation of application Ser. No. 07/865,552 filed on Apr. 9, 1992, now abandoned.

FIELD OF THE INVENTION

The present invention relates to a monoclonal antibody which suppresses the motility of cancer cells. The present antibody show suppressing activity to the motility of human cancer cells such as lung carcinoma cells and glioblastoma cells, and can be used in prophylaxis or treatment of cancer.

The present invention also relates to polypeptides and a method of producing the same. More particularly, the invention relates to polypeptides influencing the motility of cancer cells. Said polypeptides can be used in preventing the metastasis of cancer cells, in particular lung carcinoma, glioblastoma and other metastatic cancers.

BACKGROUND OF THE INVENTION

Recently, the number of deaths due to cancer is increasing year by year. On the other hand, therapeutic means have been developed rapidly against cancers and therapeutic methods for some kinds of cancer have been established.

Especially, many kinds of anti cancer antibodies have been prepared and used as a therapeutic or diagnostic drug, since the publication of Köhler and Milstein about production of monoclonal antibodies [Köhler, G. and Milstein, C., Nature, 256, 495 (1975)]. These antibodies are used for antibody missile therapy in which antibody specifically binds to cancer cells and exclude or injured them without injuring normal tissues, and show some degree of success in the therapy of blood cancer such as leukemia or lymploma.

However, few effective preventive methods are available at present against metastatic cancers. Factors affecting cancer metastasis presumably include the cell molecule surface, cell skeleton, protease and so forth. Other factors so far reported to be involved in the metastatis of cancer cells have been clarified in detail, for example metastasis-promoting factors, there are the autocrine motility factor (AMF) [Proc. Natl. Acad. Sci. USA, 83, 3302–3306 (1986)] and the chemotactic factor [Igaku no Ayumi (Advances in Medicine). 150, 805–806 (1989)]. However, cancer matastasis involves a very complicated process and therefore before the whole picture thereof is far from clarified. Under the present conditions, the use of an in vitro experimental cancer metastasis model system is thought to be most efficient in developing an agent capable of inhibiting cancer metastasis. A method comprising counting cells passing a filter (Nucleopore) having uniform pores of 5–8 μm in pore size using a chemotaxischamber is in wide use as such a system.

In the treatment of cancer, some effective therapeutic means have been established against specific kinds of cancer. However, the metastasis of cancer is difficult to prevent and at present no effective therapeutic means is available therefor.

SUMMARY OF THE INVENTION

Under these technical backgrounds, the present inventors succeeded using the above experimental system in obtaining a desirable anti-human cancer monoclonal antibody capable of suppressing the motility of cancer cells. Said antibody specifically binds to the cancer cell surface protein to thereby suppress the motility of cancer cells. Therefore it is presumable that the protein recognized by said antibody should perform an important role in the motility of cancer cells. And such as a protein or a peptide fragment thereof might very useful as a cancer metastasis preventing agent.

Making full use of genetic engineering techniques, the present inventors completed the present invention by determining the amino acid sequence of the peptide recognized by the above-mentioned monoclonal antibody, isolating a cDNA coding for the antigen, further constructed a plasmid comprising said cDNA, preparing a transformant by transformation with said plasmid and recovering the desired peptide from a culture broth of said transformant.

Thus the present invention relates to (1) an anti cancer monoclonal antibody (hereinafter sometimes abbreviated as MoAb) which prevents the motility of human cancer cells. More particularly, the present antibody is a monoclonal IgG, preferably IgG, antibody specific to a human cancer cell such as lung carcinoma cell or glioblastoid cell and recognizes a peptide which participates in the motility of cancer cell as an antigen. (2) a polypeptide containing the amino acid sequence of SEQ. ID No. 1 [hereinafter such polypeptide shall be referred to as M]; wherein M can be recognizable by the antibody (1) above, (3) a polypeptide having a partial amino acid sequence taken from the amino acid sequence of SEQ, ID No. 1 and capable of suppressing the motility of cancer cells, wherein the polypeptide (3) above may be any one provided that it has a partial amino acid sequence taken from the amino acid sequence of SEQ. ID No. 1 and shows a cancer cell motility suppressing activity, for example a polypeptide having the sequence covering the amino acid residues of 35–60, 113–142, 131–166, or 163–191, said polypeptide being selected either from a site performing a receptor function or from a site interacting another protein on the cell membrane and extracellularly; (4) a recombinant DNA comprising a nucleotide sequence coding for M; (5) a vector comprising the DNA mentioned above (4); (6) a transformant as transformed with said vector; and (7) a method of producing M which comprises cultivating a transformant as transformed with a vector comprising the DNA mentioned above (4), producing and accumulating of M in the culture broth and harvesting the same.

BRIEF DESCRIPTION OF THE DRAWINGS

FIGS. 4A and 4B show the nucleotide sequence of cDNA of the positive clone obtained in Example 7 and the amino acid sequence deducible from the nucleotide sequence.

BRIEF DESCRIPTION OF THE INVENTION

Figure 1:
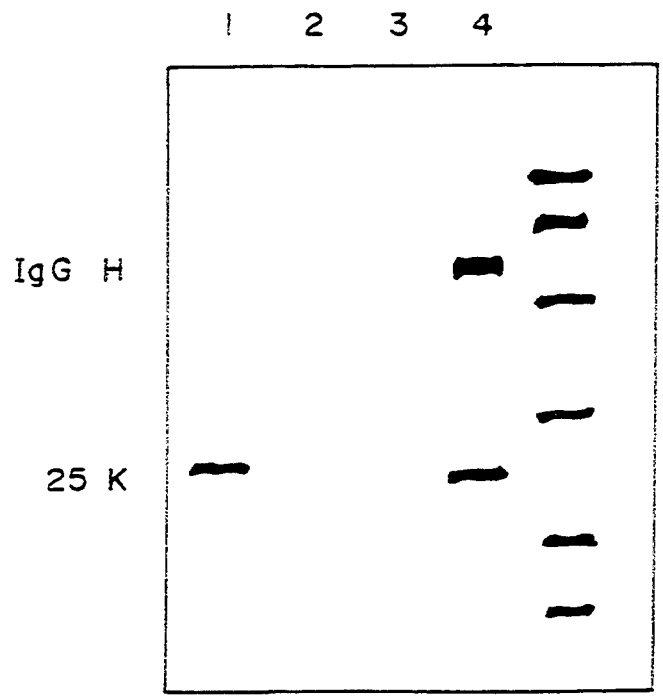
FIG. 1 shows the results of Western blotting analysis (see Example 4).

Any DNA comprising a nucleotide sequence coding for the amino acid sequence of SEQ. ID No. 1 may be used as the recombinant DNA mentioned above. However, a DNA comprising the nucleotide sequence of SEQ. ID No. 2 is preferable, for instance.

The antibodies of this invention can be used in the treatment of cancer, particularly in the prevention of cancer metastasis, either alone or combination with substances Which inhibit the adhesion of cancer cells and other metastasis inhibiting substances showing different mechanisms of action.

When bound to an appropriate antitumor substance, for example an anticancer chemotherapeutic agent such as methotrexate, daunomycin, vincristine or cisplatin, a toxin protein such as *Pseudomonas aeruginosa* exotoxin A, ricin, abrin, diphtheria toxin or neocarzinostatin, or a cytotoxin such as tumor necrosis factor, lymphotoxin or interferon, the antibodies of this invention can be used as agents for missile therapy for the treatment of cancer. In this instance, the antibodies of this invention are more advantageous in cancer therapy than the conventional missile therapy agents because an antitumor substance which will not inhibit the action of the antibodies of the present invention can be combined therewith to specifically kill cancer cells while preventing cancer metastasis.

The antibodies of this invention can be obtained from among anti-human cancer antibodies, which are produced by anti-human cancer antibody-producing hybridomas produced by a known method, by screening using the cancer cell motility suppressing activity as an index. Such anti-human cancer antibody-producing hybridomas may be of any kind provided that they can produce antibodies which specifically bind to human cancer cells. Such hybridomas include the anti-human transferrin receptor (hereinafter sometimes abbreviated as hTfR) monoclonal antibody-producing mouse hybridoma 22C6 [IFO 50172, FERM BP-2054] [cf. Japanese Unexamined Publication No. 79970/1990] or the anti-human kidney cancer monoclonal antibody-producing mouse hybridoma RCS-1[IFO 50184, FERM BP-2333] [cf. WO 91/09134], for instance.

For producing these antibody-producing hybridomas, the conventional method of hybridoma production can be used [G. Köhler et al.: Nature, 256, 495 (1975)]. In a preferred method, animals are immunized with cancer cells in the conventional manner and antibody-producing cells therefrom obtained are fused with myeloma cells or the like. Preferred cancer cells to be used for immunization, include kidney cancer cells (AM-RC-3, AM-RC-6, AM-RC-7, SK-RC-1, SK-RC-9, SK-RC-18), bladder cancer cells (T-24, KK-47, MGH-U-1), prostate cancer cells (DU-145), stomach cancer cells (NUGC-2, NUGC-3, NUGC-4, MKN-28, KATO III, MRK-1), intestinal cancer cells (SW-403, SW-620, SW-1116, SW-1222, CaOV-4, HT-29), cervical cancer cells (ME-180), melanoma cells (SK-MEL-33, SK-MEL-37), breast carcinoma cells (MCF-7), glioma cells (MG-178), lung carcinoma cells (Luci-10, Calu-6, PC-10, ADLC-DA, SBC-3, SCLC-SA, Luci-6, CADO-LC3, OKADA, QG-56), T-cell leukemia cells (CCRF-CEM, HPB-ALL, HSB-2, HUT-102, RPM-I8402, HUT-78, P12/Ichikawa, MT-1, MT-2), B-cell leukemia cells (Raji, Daudi, BALL-1, RPMI-1788, Ly-16), null cell leukemia cells (NALL-1, NALM-6, NALM-18, KOPN-K, P30/Ohkubo), myeloid leukemia cells (HL-60) and so on.

Cancer cell lines established from cancer tissues of actual cancer patients, such as lung cancer patients, for example MAC8, can also be used in accordance with the present invention.

Further, the yield of the antibodies of this invention can be increased by using, as an immunogen, a cell surface antigen recognizable by the antibodies of this invention. For differentiating such a cancer cell surface antigen, it is now a general practice to use FACS developed recently in addition to the conventional fluorescent antibody technique. When the cancer cells used are adherent cells, a cell suspension is generally prepared using phosphate-buffered saline (PBS) containing 5 mM EDTA. Trypsin, collagenase or the like may also be used as the case may be. These procedures can be carried out as described, for example, in a monograph [Zoku Seikagaku Jikken Koza (Experiments in Biochemistry, Second Series), vol. 5, Men'eki Seikagaku Kenkyuho (Methods in Immunobiochemistry), page 122, Tokyo Kagaku Dozin].

The animals to be immunized include, among others, mammals (e.g. human, mouse, rat, guinea pig, cat, dog, monkey, rabbit, sheep, goat, hamster, etc.) and birds (e.g. chicken, goose, duck, etc.). Among them, the mouse, rat and rabbit are preferred. For MoAb production, the mouse is particularly preferred.

The antibody-producing cells derived from immunized animals may be derived from the spleen, lymphatic node or peripheral blood lymphocyte system. Splenocytes are particularly preferred.

In preferred embodiments of the present invention antibody-producing cells, in particular splenocytes, are prepared by immunizing mice (4 to 10 weeks of age) with cancer cells. The method of immunization generally comprises suspending viable cells washed with phosphate-buffered saline (hereinafter sometimes abbreviated as PBS) in a small amount of PBS and administering the suspension to the mice subcutaneously at the back or abdomen or intraperitoneally in a dose of $10^6$ to $10^8$ cells/0.1 ml, preferably about $10^7$ cells/0.1 ml. Then, cells are administered in the same manner 2 to 5 times at 2-week intervals. The last immunization is performed by intravenous administration. Three to four days after the last immunization, splenocytes can be prepared from the mice in the conventional manner.

Stable production of antibodies becomes possible when these antibody-producing cells are fused to proliferative cells to give hybridomas. Myeloma cells (e.g. NS-1, P3-X63-AgUI, X45, SP2, X68-Ag8, etc.) are particularly preferred as proliferative cells with the antibody producing cells for fusion.

In particular, the MOPC21 (BALB/c mouse)-derived myeloma cell line X68-Ag8 and modifications thereof are preferred. For monoclonal antibody production, it is advantageous to use a cell line selected from among these modifide cell lines and other myeloma-derived cell lines, since cell lines of this kind are resistant to 8-azaguanine and are deficient in hypoxanthine guanine phosphoribosyltransferase and therefore cannot grow in HAT medium (containing hypoxanthine, aminopterine and thymidine). The qualities facilitate hybridoma selection after fusion.

The cell fusion is carried out by a known method and polyethylene glycol (hereinafter sometimes abbreviated as PEG), Sendai virus or the like, preferably, PEG an average molecular weight of about 1,000 to 6,000, more preferably PEG 4000 at a concentration of about 10 to 80%, preferably about 40 to 50% is particularly, is used as fusion agent.

For cell fusion, antibody-producing cells and myeloma cells are washed with RPMI1640 medium and mixed generally in a ratio of 2:1 to 10:1, and the mixture is centrifuged at room temperature and $700 \times g$ to give a cell pellet. The cell pellet is loosened with warming in a constant-temperature vessel maintained at 37° C. and a PEG solution warmed in advance is gradually added with sufficient stirring. Generally, PEG is used in an amount of 1 ml per $10^8$ cells but this amount may varies on the case-by-case basis. Then, RPMI1640 medium warmed in advance is gradually added dropwise with stirring to thereby lower the PEG concentration. Generally, 1 to 30 ml of medium is added over about 10 minutes. Cells are collected by centrifugation at room temperature and suspended in a medium containing 10% fetal calf serum (hereinafter sometimes abbreviated as FCS) to a cell concentration of 1 to $2 \times 10^6$ cells/ml, and the suspension is distributed in 100 $\mu$l portions into wells of 96 well plates. After overnight standing, a medium containing HAT and 10% FCS (HAT medium) is added (100 $\mu$l per well). A suspension of cells after cell fusion may also be directly sowed in said HAT medium for practical operation. Medium exchange is made several times during a period of 2 to 3 weeks. The method of medium exchange generally comprises removing 100 to 200 $\mu$l of medium from each well and adding 100 to 200 $\mu$l of fresh HAT medium to each well. As soon as hybridoma appearance are observed during said period, the well or wells are submitted to an appropriate screening system to detect in which the desired antibody-producing hybridoma. The hybridomas obtained are immediately subjected to cloning by an appropriate method.

For screening out such anti-cancer cell antibody-producing hybridomas, various known methods can be used, for example the mixed hemagglutination method (hereinafter sometimes abbreviated as MHA) which is based on the adsorption of indicator erythorycetes to cancer cells, the immune adherence reaction method based on the phenomenon that erythorycetes adhere to cancer cell-bound antibodies via a complement, the immunofluorescence method (hereinafter sometimes abbreviates as IF) comprising staining cancer cells with a fluorescein-labeled second antibody, generally anti-immunoglobulin antibody, followed by fluorescence analysis, or, for the screening of monoclonal antibodies against cancer cells, for example lung carcinoma cells, adhering to the microplate, the lung carcinoma cell line (e.g. A549SA) method. Antibody activity-positive hybridomas are immediately subjected to cloning, which is generally carried out with ease by the limiting dilution method, for instance. The culture supernatant of each cloned hybridoma is assayed for its antibody titer by the method mentioned above. Hybridomas stably producing a high-titer antibody are selected and further subjected to screening for detecting antibodies capable of suppressing the cancer cell motility. Said screening is carried out, for example, by the modified Boyden chamber assay using the Nucleopore membrane filter mentioned above [J. Immunol. Methods, 33, 239–247 (1980)] or by using commercially available Transwell plates (Costar). For this screening, filters with a pore size of 5 $\mu$m to 8 $\mu$m, for instance, may be selected depending on experiment conditions. Melanoma cells, glioma cells and the like are generally used as the target cancer cells but appropriate cells screened out from among other cancer cells may be used as well. For instance, MAC10 cells screened out from among lung carcinoma cells may be used. Desired monoclonal hybridomas can be obtained by selecting, in this manner, hybridomas producing an antibody showing potent inhibitory effect on cancer cells.

The production and accumulation of said anti human cancer cell monoclonal antibodies is effected by cultivating the hybridomas of this invention generally in a liquid medium, preferably a serum-free medium, or in the peritoneal cavity of a warm-blooded animal other than human (generally, mouse). When a high-purity antibody is particularly required, a serum-free medium should desirably be used. Examples of such cultivation are given below.

As the liquid medium, there may be mentioned, for example, a basal medium for animal cell culture [e.g. an equivolume mixture ($^I$.H medium) of Iscove medium and Ham's F-12 medium, or RPMI1640 medium] supplemented with fetal calf serum, or GIT medium (Wako Pure Chemical Industries) (cf. Japanese Unexamined Publication No. 145088/1985). The cultivation is generally carried out at about 30° C. to about 38° C., preferably about 37° C., for about 3 to about 60 days, preferably about 5 to about 10 days.

For the transplantation into the mouse peritoneal cavity, about $2 \times 10^5$ to about $5 \times 10^7$, preferably about 1 to about $5 \times 10^6$, antibody-producing hybridoma cells are introduced into the peritoneal cavity of each mouse, whereby 3 to 10 ml of an ascitic fluid containing a quantity of an antibody is obtained after about 10 to about 35 days of feeding.

The antibody in the liquid medium or ascitic fluid can be purified using a combination of known biochemical techniques. For example, the antibody-containing liquid is centrifuged, and the supernatant is subjected to salting out (generally, with ammonium sulfate or sodium sulfate). The protein precipitate obtained is dissolved in an appropriate buffer solution, dialyzed and subjected to column chromatography (using a DEAE ion exchange column, hydroxyapatite column, gel filtration column, protein A column, protein G column, or the like) or immunoaffinity chromatography, for instance, for separating and purifying the desired antibody. Such a separation and purification procedure can give about 5 to about 30 mg of an anti-cancer cell MoAb with a purity of not less than 90% (on the protein weight basis) from, for example, 500 ml of liquid medium. Similarly, 50 ml of ascitic fluid gives 10 to 200 mg of such antibody. In particular, an antibody with a higher purity can be obtained by combining column chromatography using protein A or protein G with chromatography using a gel filtration column carrier, DEAE ion exchange column carrier, hydroxyapatite or the like. These purified antibody preparations have a heterologous protein content of not more than about 0.1% and are suited for administration to humans as drugs.

Upon treatment with a proteolytic enzyme (e.g. papain, pepsin) or reductive treatment, the monoclonal antibodies obtained in the above manner can give Fab, Fab' or F(ab')$_2$ fragments while the ability to bind to cancer cells is retained. Such fragments can be used for the same purposes as the MoAb of this invention. When said hybridomas produce mouse IgG MoAb, it is possible to produce a mouse-human chimera antibody by isolating a DNA coding for the antigen recognition site-containing variable region of said anti-cancer cell MoAb and joining thereto a gene coding for the constant region of human IgG using the gene manipulation technique [Steplewski, Z. et al.: Proc. Natl. Acad. Sci. USA, 83, 4852 (1988)]. Such a chimera antibody is advantageous in administering to humans because of its low antigenicity. After sterilization by filtration using a membrane filter or the like, the anti-cancer cell monoclonal antibodies of the present invention can be used either alone or admixed with pharmacologically acceptable appropriate carriers, excipients, diluents or the like to give pharmaceutical compositions such as injectable solutions. Such MoAb preparations, as anticancer agents, can produce the cancer metastasis-inhibiting effect and, when bound to an appropriate anti-cancer agent, can be used as the therapeutic drugs known as missile therapy agents.

The present antibody is useful for detecting human cancer cells, especially human lung carcinoma cells or human grioblastona cells, as well as other anti cancer antibodies.

Further, the present antibody is also useful for screening or purification M of the present invention.

The M of the present invention can be produced by a combination of known genetic engineering techniques.

Namely, an expression vector comprising a DNA having the nucleotide sequence coding for M can be produced, for example, by (i) isolating a phage containing the desired DNA by means of a proto blot immunoscreening system using an appropriate cDNA library, (ii) excising the desired cloned DNA from said phage and (iii) joining said cloned DNA toga vehicle at a site downstream from the promoter in said vehicle.

As the vector, there may be mentioned *Escherichia coli*-derived plasmids (e.g. pBR322, pBR325, pUC12, pUC13), *Bacillus subtilis*-derived plasmids (e.g. pUB110, pTB5, pC194), *Saccharomyces cerevisiae*-derived plasmids (e.g. pSH19, pSH15), bacteriophages such as phage, and animal viruses such as retroviruses and vaccinia virus, among others.

Said gene may has ATG as the translation initiation codon at its 5' end and it may also have TAA, TGA or TAG as the translation termination codon at its 3' end. For expression of said gene, a promoter is joined to said gene upstream therefrom. Any promoter that is appropriate to the host employed for gene expression may be used as the promoter in the practice of the invention.

When the host to be transformed is *Escherichia coli*, the T7 promoter, trp promoter, lac promoter, rec promoter, $\lambda P_L$ promoter, lpp promoter and the like are for instance, preferred. And when the host is *Bacillus subtilis*, the SPO1 promoter, SPO2 promoter, penP promoter and the like are, for instance, preferred; and when the host is a yeast, the PHO5 promoter, PGK promoter, GAP promoter, ADH promoter and the like are, for instance, preferred. It is particularly preferred that the host is *Escherichia coli* and the promoter is the trp promoter or $\lambda P_L$ promoter.

When animal cells are used as the host, preferred promoters include SV40-derived promoters and retrovirus promoters, among others. In particular, SV-40-derived promoters are more preferred.

A transformant is produced using the thus-prepared DNA-comprising vector.

Preferred host include, there may be mentioned prokaryotes such as *Escherichia coli, Bacillus subtilis* and actinomycetes as well as eukaryotes such as yeasts, fungi and animal cells.

As representative examples of the above-mentioned *Escherichia coli*, there may be mentioned, such as *Escherichia coli* K12 DH1 [Proc. Natl. Acad. Sci. USA, 60, 160 (1968)], JM103 [Nucl. Acids Res., 9, 309 (1981)], JA221 [J. Mol. Biol., 120, 517 (1978)], HB101 [J. Mol. Biol., 41, 459 (1969)]and C600 [Genetics, 39, 440 1954]; and, as examples of the *Bacillus subtilis* mentioned above, there may be mentioned such as *Bacillus subtilis* MI114 [Gene, 24, 255 (1983)] and 207-21 [J. Biochem., 95, 87 (1984)].

Representative examples of the above-mentioned yeasts include, among others, *Saccharomyces cerevisiae* AH22, AH22R', NA87-11A and DKD-5D.

Representative examples of the animal cells mentioned above include the simian COS-7 and Vero cells, chinese hamster CHO cells, and murine L cells, among others.

The transformation of the above-mentioned *Escherichia coli* is performed by the method described in Proc. Natl. Acad. Sci. USA, 69, 2110 (1972) or in Gene, 17, 107 (1982), for instance.

The transformation of *Bacillus subtilis* is carried out by the method described in Molec. Gen. Genet., 168, 111 (1979), for instance.

For the transformation of yeasts, the method described in Proc. Natl. Acad. Sci. USA, 75, 1929 (1978), for instance, is followed.

For transforming animal cells, the method described in Virology, 52, 456 (1973), for instance, is followed.

In this manner, a transformant as transformed with a vector comprising a DNA coding for M is obtained.

In cultivating the transformant derived from a host such as *Escherichia coli, Bacillus subtilis,* an actinomycete, a yeast and a fungus, a liquid medium is suitable for the cultivation. And the carbon sources, nitrogen sources, inorganic substances and other substances that are required for the growth of said transformant are contained in said medium. The carbon sources include, among others, glucose, dextrin, soluble starch, and sucrose. The nitrogen sources include, among others, such inorganic or organic substances as ammonium salts, nitrate salts, corn steep liquor, peptone, casein, meat extract, soybean cake and potato extract. The inorganic substances include calcium chloride, sodium dihydrogen phosphate, and magnesium chloride, among others. The medium preferably has a pH of about 5 to about 8.

When the host is *Escherichia coli*, M9 medium containing glucose and casamino acids [Miller, J.: Experiments in Molecular Genetics, page 431, Cold Spring Harbor Laboratory, New York, 1972] is preferred as the medium. Generally, the cultivation is carried out at about 14° C. to about 43° C. for about 3 to about 24 hours, with aeration and/or agitation may be performed when necessary.

When the host is *Bacillus subtilis,* the cultivation is generally conducted at about 30° C. to about 40° C. for about 6 to about 24 hours, and aeration and/or agitation may be conducted when necessary.

In cultivating a transformant derived from a yeast host, Burkholder's minimum medium [Bostian, K. L. et al: Proc. Natl. Acad. Sci. USA, 77, 4505 (1980)], for instance, may be used as the medium. The pH of the medium is preferably adjusted to about 5 to about 8. The cultivation is generally carried out at about 20° C. to about 35° C. for about 24 to about 72 hours, with aeration and/or agitation when necessary.

In cultivating a transformant derived from an animal cell line as the host, the medium to be used is, for example, MEM containing about 5–20% FBS [Science, 122, 501 (1952)], DMEM [Virology, 8, 396 (1959)], RPMI1640 medium [J. Am. Med. Assoc., 199, 519 (1967)], or 199 medium [Proc. Soc. Exp. Biol. Med., 73, 1 (1950)], for instance, may be used as the medium. The pH is preferably about 6 to about 8. The cultivation is generally carried out at about 30° C. to about 40° C. for about 15 to 60 hours, with aeration and/or agitation when necessary.

The production method of this invention causes production and accumulation of the M protein in the culture broth, either intracellularly or extracellularly. While the whole molecule type, M, is produced mostly within cells, it may be caused to secrete as a fused protein by attaching an appropriate leader sequence thereto in the conventional manner.

For extracting M produced intracellularly from the culture broth, cultured cells are collected by a known method and suspended in a buffer containing a protein denaturing agent as guanidine hydrochloride or urea or in a buffer containing a surfactant such as Triton X-100 and the suspension is then subjected to centrifugation to give an M-containing supernatant, or cells are disrupted by ultrasonication, treatment with an enzyme such as lysozyme, or freeze-thawing method and then the resultant mixture is centrifuged to give an M-containing supernatant. Any other appropriate extraction method may also be used.

For separating and purifying M contained in such a supernatant or formed and accumulated extracellularly, a suitable combination of known separation and purification methods may be employed. Such known separation and purification methods include those which utilize differences in solubility, such as salting out and solvent-caused precipitation, those which essentially utilize differences in molecular weight, such as dialysis, ultrafiltration, gel filtration and SDS-polyacrylamide gel electrophoresis, those which utilize the specific affinity, such as affinity chromatography, those which utilize differences in hydrophobicity, such as reversed-phase high-performance liquid chromatography, those which utilize differences in isoelectric point, such as electrofocusing, and so forth. In particular, since M is an antigen to the monoclonal antibody M31-15, immunoaffinity chromatography using said monoclonal antibody is very efficient for the purification of said protein.

On the other hand, M of the present invention and partial peptides thereof can also be chemically synthesized, for example using an automated peptide synthesizer. The basic synthetic process and other conditions are essentially as described by R. B. Merrifield [Advances in Enzymology, 32, 221–296(1969)]. The principle of this method consists in covalently binding the carboxyl-terminal amino acid to a carrier resin and extending the peptide chain toward the amino terminal by successively repeating elimination of the α-amino-protecting group and condensation with a protected amino acid to give a peptide-resin having the desired amino acid sequence. The condensation of each amino acid, the elimination of the α-amino-protecting group and other treatment are carried under substantially the same conditions without intermediate purification, so that, generally, high-level skill is not required for the synthesis. Moreover, this method can be performed speedily and is very convenient for the synthesis of various peptides. The thus-obtained peptide-resin is treated, for example, with anhydrous hydrogen fluoride, trifluoromethanesulfonic acid or trifluoroacetic acid, in the presence of a variety of additives, whereby the splitting off of the peptide from the resin and the removal of all the remaining protective groups can be realized simultaneously in one step.

The thus-obtained crude peptide can be purified by known means for purifying peptides or proteins, for example by gel filtration, ion exchange chromatography using a cation or anion exchange resin or, further, any of column chromatography or high-performance liquid chromatography techniques based on various principles, such as hydrophobic chromatography, partitive adsorption chromatography, etc.

The thus-obtained polypeptide of the present invention can be used in the form of various salts. As the salts, there may be mentioned, for example, salts with inorganic acids or with organic acids such as formic acid, acetic acid, tartaric acid citric acid, and salts with inorganic bases such as sodium and ammonia or with organic bases such as triethylamine, ethylamine and methylamine.

The thus obtained polypeptide of the invention can be used as a therapeutic agent.

For the therapeutic use of the polypeptide of the invention as a drug, it may be safely administered either alone as such in the form of a powder or together with a pharmacologically acceptable carrier, excipient or diluent, namely in the form of a pharmaceutical composition (e.g. injection, tablet, capsule, liquid, ointment), non-orally or orally to warm-blooded animals (e.g. human, mouse, rat, hamster, rabbit, dog, cat).

Injectable solutions can be prepared in the conventional manner using, for example, physiological saline or an aqueous solution containing glucose and/or other auxiliary agents. Pharmaceutical compositions such as tablets and capsules can also be prepared in the conventional manner.

When the polypeptide of the invention is used as the above-mentioned drug, it is administered, for example to the warm-blooded animals mentioned above at an appropriate daily dose within the range of about 1 μg to about 1 mg/kg as selected in consideration of the route of administration, symptom and other factors.

In the present specification and drawings, the abbreviations used for representing nucleotide, amino acids and others are those employed by the IUPAC-IUB Commission on Biochemical Nomenclature or in conventional use in the relevant field of art. A partial listing thereof is given below. In case optical isomerism is possible for an amino acid, it is to be understood that said amino acid is in the L form unless otherwise specified.

Unless otherwise specified, the direction of from left to right in each sequence corresponds to the direction of from the N terminus to the C terminus as for amino acid sequence and with the direction of from the 5' end to the 3' end as for a nucleotide sequence.

The amino acid sequence of M may be partially (e.g. up to about 5%) modified (e.g. by addition, deletion, or substitution by another or other amino acids).

DNA : deoxyribonucleic acid
cDNA : complementary deoxyribonucleic acid
A : 2'-deoxyadenylic acid residue
T : thymidylic acid residue
G : 2'-deoxyguanidylic acid residue
C : 2'-deoxycytidylic acid residue
RNA : ribonucleic acid
mRNA : messenger RNA
dATP : deoxyadenosine triphosphate
dTTP : deoxythymidine triphosphate
dGTP : deoxyguanosine triphosphate
dCTP : deoxycytidine triphosphate
ATP : adenosine triphosphate
EDTA : ethylenediaminetetraacetic acid
SDS : sodium dodecyl sulfate
FBS : fetal bovine serum
Gly or G : glycine
Ala or A : alanine
Val or V : valine
Leu or L : leucine
Ile or I : isoleucine
Ser or S : serine
Thr or T : threonine
Cys or C : cysteine
Met or M : methionine
Glu or E : glutamic acid
Asp or D : aspartic acid
Lys or K : lysine
Arg or R : arginine
His or H : histidine
Phe or F : phenylalanine
Tyr or Y : tyrosine
Trp or W : tryptophan
Pro or P : proline
Asn or N : asparagine
Gln or Q : glutamine

EXAMPLE

The following Reference Examples and Working Examples are further illustrative of the present invention but are of course by no means limitative of the scope thereof.

The hybridomas or transformant cells obtained in the following Reference Examples or Working Examples have been deposited at the Institute for Fermentation, Osaka (IFO; 17-85 Juso-honmachi 2-chome, Yodogawaku, Osaka) and Fermentation Research Institute, Ministry of International Trade and Industry (FRI; 1-3 Higashi 1-chome, Tsukuba, Ibaraki Prefecture) under the Budapest treaty respectively as shown in the following table.

|  | IFO (IFO No.) | FRI (FERM BP No) |
|---|---|---|
| Mouse hybridoma M31-15 | 50324 (1991.4.2) | 3340 (1991.4.9) |
| E.coli DH5αF'IQ/pTB1352 | 15165 (1991.4.9) | 3357 (1991.4.15) |
| Hamster fibroblast CHO/M-1 | 50365 (1992.1.31) | 3746 (1992.2.13) |
| E.coli DH1/pTB1442 | 15259 (1992.2.5) | 3745 (1992.2.10) |

In the above table the numbers in ( ) show the date of deposition

Reference Example 1 Establishment of the cell line

MAC8

A cancer tissue slice excised from a human lung carcinoma patient was rinsed with phosphate buffered saline (PBS) (137 mM NaCl, 2.7 mM KCl, 8.1 mM $Na_2HPO_4$, 1.5 mM $KH_2PO_4$; pH 7.4) and then cut to pieces 1 to 2 mm square in size by means of scissors. The pieces obtained were subcutaneously transplanted into nude mice and, after 1 to 2 weeks, tumor tissues were excised from those nude mice that showed tumor growth. The tumor tissues were rinsed with PBS, then cut to pieces 1 to 2 mm square in size using scissors and subjected to digestion with PBS containing 0.25% trypsin for 10 minutes. The first digestion liquid was discarded and the second and third digestion liquids were pooled and centrifuged (700×g, 5 minutes). The thus-obtained cells were rinsed with RPMI1640 medium containing 10% FBS and then cultured in the same medium, whereby a human lung carcinoma cell line, MAC8, was established. The thus-established cell line was 10 then subjected to cloning by the limiting dilution method. Reference Example 2 ELISA of anti cancer antibodies The lung cancer cell line MAC8 established in Reference Example 1 was suspended in RPMI1640-10% FBS medium in a concentration of $4 \times 10^5$ cells/ml, and the suspension was distributed in 100 µl portions into wells of a 96 well microplate and cultured overnight in a $CO_2$ incubator maintained at 37° C. On the next day, the plate was rinsed with three portions of 50 mM Tris buffer (pH 7.4), then test culture supernatants were respectively distributed in 100 µl portions in wells of the plate, and the plate was incubated at 37° C. for 1 hour. The plate was rinsed four times and then subjected to reaction with biotinylated goat anti mouse immunoglobulin for 1 hour. The plate was rinsed four times, avidin-biotinylated peroxidase (Vectastatin) was added to each well and the reaction was allowed to proceed for 1 hour. The plate was rinsed four times, 50 µl of an orthophenylenediamine solution (1 mg/ml, 0.5 µl aqueous hydrogen peroxide, 5.1 mg citric acid, 18.4 mg $Na_2HPO_4 \cdot 12H_2O$/ml) was added to each well, and the plate was allowed to stand for 10 minutes for color development. Then, 100 µl of 2 N $H_2SO_4$ was added to each well, and the absorbance of each well was measured at 450 nm using an optical densitometer for 96 well microplates.

Example 1 Production of monoclonal antibodies (1) Preparation of mouse splenocytes The MAC8 cell suspension ($1 \times 10^7$ cells/0.2 ml/mouse) in PBS as obtained in Reference Example 1 was intraperitoneally administered to Balb/c mice (8 week-old females) and booster was performed after 2, 3 and 4 days and after 7 weeks. The immunization at 7 weeks was carried out in the manner of intravenous administration. Three days after the last immunization, the spleen was excised from each mouse and a splenocyte suspension was prepared aseptically.

(2) Cell fusion

The mouse splenocyte suspension ($2 \times 10^8$ cells) obtained as described under (1) was mixed with a suspension of the mouse myeloma cell line SP2 ($5 \times 10^7$ cells), and the mixture was centrifuged at 700×g for 5 minutes to give a cell pellet. To the cell pellet was added dropwise and gradually 1 ml of a 50% solution of polyethylene glycol 4000 (Sigma Chemical Island, NY) over 2 minutes with stirring. The polyethylene glycol concentration was gradually lowered by successive addition of 1, 1.5, 2, 3, 4 and 5 ml of RPMI1640 medium at 2 minute intervals. The resultant mixture was centrifuged at 700×g for 5 minutes. The cells thus collected were washed with RPMI1640 medium and then suspended in RPMI1640 medium supplemented with 10% FBS/HAT ($10^7$ cells/ml), and the suspension was distributed in 100 μl portions into wells of 96 well plates. After 2, 5 and 10 days, the half of the medium was replaced with fresh HAT medium and, on day 21, 100 μl of the culture supernatant was taken from each well and subjected to antibody screening by ELISA as described in Reference Example 2.

(3) Limiting dilution method

Each hybridoma screened out as described above under (2) was cultured in HAT medium, the culture was diluted to a cell count of 5 cells/ml, and the dilution was distributed in 100 μl portions into wells of a 96 well tissue culture plate and cultured. The culture fluids in those wells where single colony growth was observed were examined for antibody-producing ability by ELISA as described in Reference Example 2. Unique clone cells were thus obtained.

(4) Screening for a cancer cell motility suppressing antibody

A 0.6 ml portion of the culture supernatant of the hybridoma obtained in above (3) was added to the lower chamber portion of a Transwell plate, 0.1 ml of a suspension of the lung carcinoma cell line MAC10 ($5 \times 10^5$/ml; RPMI1640-10% FBS) was placed on a Nucleopore membrane filter (pore size 5 μm), and cultivation was carried out in a $CO_2$ incubator at 37° C. for 16 hours. Those cells that had passed through the Nucelopore membrane filter and settled on the bottom of the plate were counted using a phase contrast microscope. In this way, 135 hybridomas obtained in above (3) were screened and a mouse hybridoma M31-15 showing a potent inhibitory activity was selected.

(5) Preparation of an antibody

Five BALB/c mice (10 week-old females) were intraperitoneally administered with 0.1 ml of pristane (mineral oil; Wako Pure Chemical Industries Ltd.) and, after 2 weeks, intraperitoneally given 0.5 ml of a suspension of the hybridoma M31-15 ($2 \times 10^7$ cells/ml). After 14 days, the ascitic fluid was recovered from the mice, centrifuged at 1,500 rpm for 10 minutes to thereby remove cells, further centrifuged at 18,000 rpm for 60 minutes, and then passed through a glass filter (Whatman GF/C) and a Milex GV filter (0.22 μm, Millipore) for sterilization by filtration, whereby the ascitic fluid was obtained in a yield of 28.5 ml.

For purifying the IgG antibody from the ascitic fluid, the MAPSII kit (protein A column; Bio-Rad) was used. Thus, 0.5 ml of binding buffer was added to 0.5 ml of the ascitic fluid, 0.5 ml of the mixture was applied to the protein A column (Affiprep; 30×4.6 mm), and elution was carried out according to the elution program given below and using a high-performance liquid chromatograph manufactured by Varian.

Elution solvent A: binding buffer;
Elusion solvent B: PBS [8.1 mM $Na_2HPO_4$, 1.5 mM $KH_2PO_4$, 137 mM NaCl, 2.7 mM KCl (pH 7.4)];
Elution solvent C: elution buffer;
Elution program; minute 0, 100% A; minute 3, 100% A; minute 3.01, 100% B; minute 15, 100% B; minute 15.01, 100% C; minute 20, 100% C; minute 20.01, 100% B;
Elution speed: 0.8 ml/min.;
Detection wavelength: 280 nm;
Loop: 1 ml.

The IgG antibody eluted from the column was immediately dialyzed against PBS and then passed through a Milex GV filter (Millipore) for sterilization by filtration, to give 0.4 mg of a purified sample of the mouse anti-human cancer antibody M31-15 ($IgG_1$).

Example 2 Specificity of the monoclonal antibody

The binding ability of the antibody M31-15 to cancer cells was estimated using FACStar (Becton Dickinson). The adherent cell line was detached with a PBS/0.02% EDTA solution containing 0.125% trypsin and washed with RPMI1640-10% FBS medium, and the cells, in a concentration of $1 \times 10^6$ cells/ml, were maintained at 0° C. for 1 hour. The purified antibody M31-15 was added (final concentration of 1 μg/ml) and the reaction was allowed to proceed at 0° C. for 1 hour. The cells were washed three times with PBS-0.1% $NaN_3$ and reacted with 100 μl of FITC-labeled anti mouse IgG (H+L) antibody (20 fold dilution) at 0° C. for 30 minutes. After washing with PBS-0.1% $NAN_3$, the cells were suspended in 2 ml of PBS-0.1% $NaN_3$ and analyzed using FACStar. The antibody M31-15 bound to most of cancer cells except Hepatocellular carcinoma and some lymphoid cancer cells (Table 1).

TABLE 1

| Cell line | Cases of staining | Positive |
| --- | --- | --- |
| Lung carcinoma | 4 | 4 |
| Gastric carcinoma | 2 | 2 |
| Pancreatic carcinoma | 2 | 2 |
| Breast carcinoma | 2 | 2 |
| Hepatocellular carcinoma | 2 | 0 |
| Colon carcinoma | 1 | 1 |
| Uterine carcinoma | 1 | 1 |
| Epidermal carcinoma | 1 | 1 |
| Melanoma | 1 | 1 |
| Glioma | 1 | 1 |
| Lymphoid cancer cells | 9 | 4 |
| Fibloblast | 4 | 2 |

Example 3 Immobilization of the antibody M31-15

A 0.48 mg portion of the purified monoclonal antibody obtained in Example 1-(6) was dialyzed overnight against 1 liter of 0.1M $NaHCO_3$ (pH 8.4). AffiGel 10 (Bio-Rad) (2 ml) was washed as directed in the relevant brochure and reacted with the antibody at 4° C. for 24 hours for immobilizing the antibody M31-15. Then, the gel was washed with 10 ml of 0.1 M Tris-HCl (pH 8.1), allowed to stand in the same buffer at 4° C. for 3 days to block remaining active groups, and then washed with PBS. A control gel was prepared by the same treatment procedure except that the buffer used was antibody-free.

Example 4 Confirmation of the antigen-binding activity of the immobilized antibody M31-15

MIA PaCa-2 cells were cultured in a roller bottle (Corning 25240) using RPMI 1640-10% FCS medium. Cells were released with a scraper, washed twice with 0.1 M Tris-HCl (pH 8.1) and then solubilized by 10 minutes of treatment on ice with 2 ml of 1% Triton X114/0.1 M Tris-HCl/10 mM EDTA/0.2 mMAPMSF/(2 U/ml) Trasylol (pH 8.1). The centrifugation supernatant (15,000 rpm, 10 minutes) was incubated at 37° C. for 10 minutes and then centrifuged at room temperature and 3,000 rpm for 10 minutes. The upper layer was discarded, 2 ml of 0.1 M Tris-HCl (pH 8.1) was added to the lower layer and the mixture was centrifuged at room temperature for 10 minutes. To the lower layer was added 0.5 ml of 1% CHAPS/0.1 M Tris-HCl (pH 8.1). The resultant mixture was centrifuged at 4° C. and 15,000 rpm for 30 minutes to give about 0.9 ml of a supernatant.

In an Eppendorf tube was placed 5 μl of the supernatant, followed by addition of 15 μl of PBS and about 10 μl of the antibody M31-15 bound AffiGel 10 obtained in Example 3. The mixture was incubated at room temperature for 1 hour and centrifuged at 3,000 rpm for 10 minutes, and the supernatant was recovered using a microsyringe and subjected to SDS-PAGE followed by Western blotting. An attempt was made to elute the antigen bound to the gel by adding 5 μl of 10% SDS, 5 μl of 1% DTT and 10 μl of electrophoretic buffer and heating in boiling water for 5 minutes. With a control gel, the antigen was not bound to the gel but recovered in the supernatant whereas, in the case of the antibody M31-15 bound gel., the antigen did not remain in the supernatant but was wholly absorbed on the gel (FIG. 1).

Experimental Example 1 Prevention of in vitro metastasis by the monoclonal antibody M31-15

MAC8 cells cultured in a flask were detached using trypsin, rinsed once with 10% FBS/RPMI1640 medium and then twice with RPMI1640, and intravenously administered to BALB/c nu/nu mice through the caudal vein at a dose of 2 or $6 \times 10^5$ cells. For evaluating the monoclonal antibody M31-15 obtained in Example 1 for metastasis preventing effect, 50 μg of M31-15 was intravenously administered through the caudal vein 3 hours after cancer cell administration. After 3 months, the colonies of cancer cells that had metastasized to the lung were counted. The results are shown in Table 2. The administration of the antibody M31-15 resulted in a significant decrease in the number of metastatic colonies.

TABLE 2

|  | Metastasis positive cases/number of cases | Average number of colonies |
|---|---|---|
| Control group | 6/7 | 54.4 |
| Antibody group | 3/4 | 1.8 |

Experimental Example 2 Motility suppression by the purified antibody M31-15

(1) Suppression of the Motility of MAC10 cells

Figure 2:
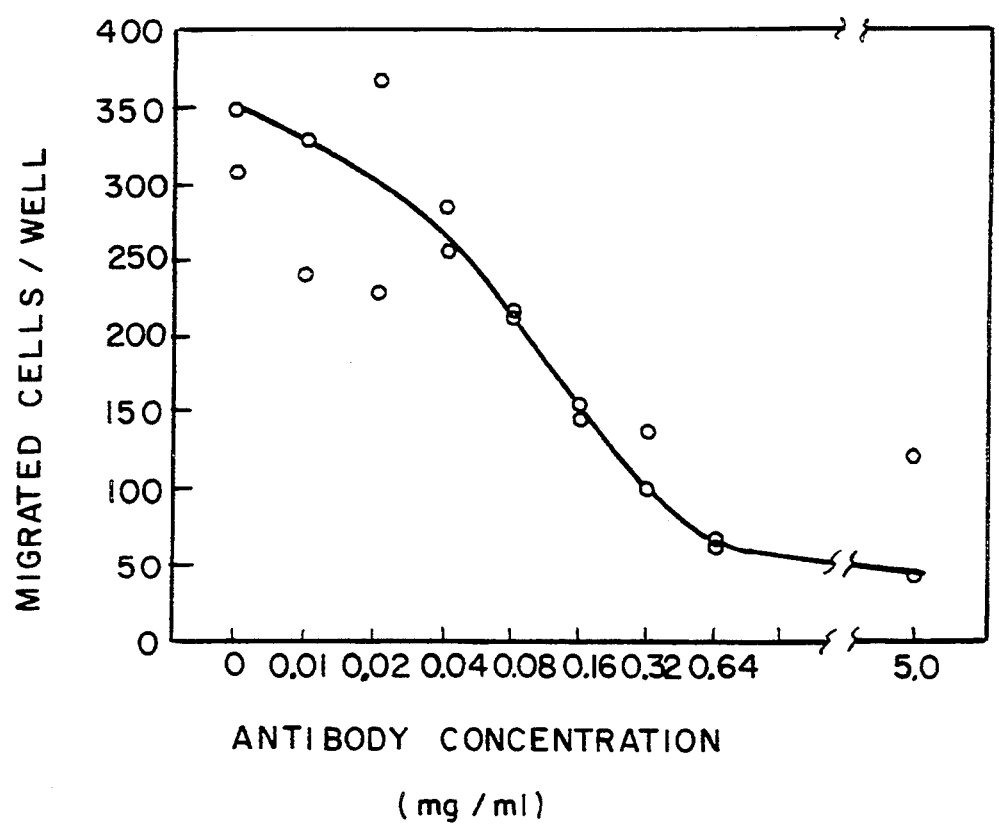
FIG. 2 shows the result concerning the suppression of the motility of MAC10 cells by the purified antibody M31-15 (see Experimental Example 2).

MAC10 cells were released from the culture flask wall using PBS containing 0.01% EDTA, washed with RPMI 1640-10% FCS medium, and suspended to a concentration of $5 \times 10^5$ cells/mi. RPMI1640-10% FCS medium and the purified antibody M31-15 (0 to 10 μg) (0.6 ml) were added to the lower chamber of the Transwell plate (Costar) and 0.1 ml of the MAC10 cell suspension to the upper chamber. After 16 hours of incubation at 37° C., cells that had migrated into the medium in the lower chamber through the membrane were collected and, after concentration by centrifugation, transferred to a 96 well microplate and counted under a phase contrast microscope. As shown in FIG. 2, 50% motility suppression was observed at an antibody concentration of 0.1 μg/ml.

(2) Suppression of the motility of T98G cells

T98G cells were grown in a 75 cm flask (Corning 25110) using MEM-10% FCS medium (supplemented with 1% nonessential amino acids and 1% sodium pyruvate. After formation of a dense monolayer of cells, the medium was discarded, cells were washed twice with the same medium as mentioned above except that it was serum-free, 3 ml of the medium was added, and incubation was conducted at 37° C. for 24 hours. The culture supernatant was collected and deprived of cells by 5 minutes of centrifugation at 1,500 rpm to give a chemotactic factor.

A mixed solution (30 μl) of the crude chemotactic factor and the purified antibody (0 to 1 μg/ml) was charged into the lower chamber of a microchemotaxis chamber (Academica), a Nucleopore membrane (PVPF) with a pore size of 8 μm was placed on said chamber, and a T98G cells suspension ($2.5 \times 10^4$ cells/50 μl) was added to the upper chamber. Incubation was conducted at 37° C. for 4 hours. Cells on the upper surface of the membrane were removed, and cells that had passed through the membrane and were adhering to the lower surface of the membrane were stained with Diff-Quick (Green Cross Corp.). Cells were counted in two visual fields (each 0.25 mm square) using an object lens of 40 magnifications. The results are shown in Table 3. At a concentration of 0.1 μg/ml, the antibody inhibited not less than 50% of the motility of T98G cells.

TABLE 3

| Chemotactic factor | Antibody M31-15 (μg/ml) | Number of migrant cells |
|---|---|---|
| − | − | 0 |
| + | — | 128 |
| + | 0.1 | 42 |
| + | 0.5 | 6 |
| + | 1.0 | 4 |

Experimental Example 3 Absorption of the chemotactic factor by the immobilized antibody M31-15

About 20 μl of the gel obtained in Example 3 was placed in an Eppendorf tube (3810) using a spatula, 0.4 ml of the crude chemotactic factor obtained in Experimental Example 2-(2) was added, and the mixture was incubated at room temperature for 1 hour and then centrifuged at 3,000 rpm for 10 minutes. The supernatant was assayed for inhibitory activity by the method described in Example 2-(2). The chemotactic factor was used in a doubling dilution series. The chemotactic factor was not absorbed (Table 4).

TABLE 4

| Chemotactic factor | Antibody-AffiGel 10* | Number of migrant cells |
|---|---|---|
| − | − | 0 |
| + | — | 194 |
| + | Incubated with MEM | 152 |
| + | + | 52 |
| + | Control gel | 95 |

*The antibody-AffiGel 10 (or control gel) was incubated with the chemotactic factor (or MEM) at room temperature for 1 hour and the supernatant was subjected to the assay.

Example 5 identification of an antigen recognized by the antibody M31-15

Figure 3:
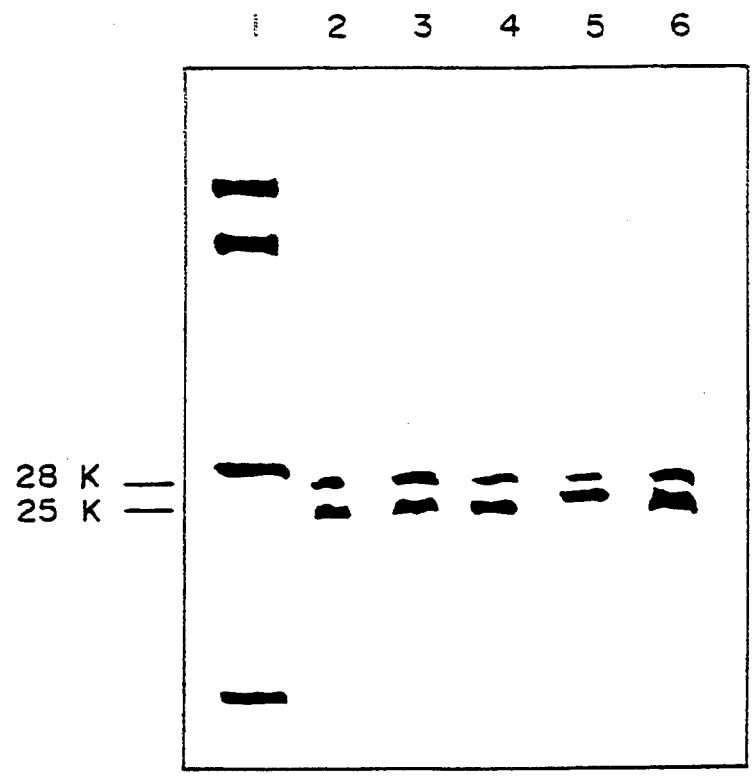
FIG. 3 shows the results of Western blotting analysis (see Example 5).

MIA PaCa-2 cells (Pancreatic carcinoma cells), HEL cells (erythroleukemia cells), ZR-75-30 cells (breast carcinoma cells), MAC10 cells (lung carcinoma cells), and AZ521 (Gastric carcinoma cells) were respectively cultured on Falcon dishes (3003) as monolayers. After two washings with 0.1M Tris-HCl (pH 8.1), cells were collected using a scraper (Costar, 3010), washed by centrifugation and then solubilized by 2 hours of treatment at 0° C. with 100 μof 1% CHAPS/0.1 M Tris-HCl/10 mM EDTA/0.2 mMAPMSF/Trasylol (2 U/ml). The supernatants obtained by 30 minutes of centrifugation at 15,000 rpm (20 μl each) were subjected to SDS-PAGE (gel concentration 12%) according to Laemmli [Nature Lond., 227,680–685 (1970)], followed by Western blotting for antigen detection. As shown in FIG. 3, all the cancer cell lines gave a main band corresponding to a molecular weight of 25,000 and a secondary band corresponding to a molecular weight of 28,000.

Example 6 Cloning of cDNA coding for M

*Escherichia coli* Y1090 attached to the λgt11 cDNA library kit (human breast carcinoma cDNA library; CLONTECH Lab. Inc.) was infected with said library and sowed onto an L broth soft agar plate. When plaque appearance began, a nitrocellulose membrane containing IPTG (isopropyl thiogalactoside) was placed on the plate, and incubation was performed for 3.5 hours. Then the nitrocellulose membrane was separated, rinsed with TBST buffer (10 mM Tris-HCl, 150 mM NaCl, 0.05% Tween 20, pH 8.0) and immersed in a 20% FBS solution for 30 minutes. The thus-treated nitrocellulose membrane was immersed in TBST containing the antibody M31-15(2 μg/ml) and an *Escherichia coli* extract (1 mg/ml) and the reaction was allowed to proceed at room temperature for 50 minutes. The membrane was washed three times with TBST buffer, then reacted with alkaline phosphatase-labeled anti mouse IgG antibody (5,000-fold diluted) for 30 minutes, and washed three times with TBST, followed by color development using substrates (Nitro-blue tetrazolium and 5-bromo-4-chloro-3-indoyl phosphate). From among $1 \times 10^6$ pfu of phage, 14 positive clones were selected. These 14 clones were rescreened by the method mentioned above. One clone was again found positive, hence said clone was selected as a positive one.

Example 7 Production of a transformant containing the plasmid pTB1352

*Escherichia coli* Y1090 was infected with the positive clone selected, then sowed onto an L broth soft agar medium and incubated at 37° C. for 16 hours. About $10^9$ pfu of phage were then extracted from the soft agar. DNA was purified from the thus-obtained phage using the QIAGEN>lambda<kit (DIAGEN GmbH). The purified DNA was digested with the restriction enzyme EcoRI, and the DNA fragment obtained was inserted into the plasmid pUC118 (Takara Shuzo) at the EcoRI site using T4 DNA ligase, whereby a plasmid, pTB1352, was constructed. The thus-obtained plasmid pTB1352 was used to transfect *Escherichia coli* DH5αF'IQ ™ to give a transformant, *Escherichia coli* DH5αF'IQ ™/pTB1352.

Example 8 Nucleotide sequence determination of DNA

The transformant obtained in Example 6 was infected with the helper phage KO-7 and then cultured in 2×YT medium (1.6% Bacto-tryptone, 1% yeast extract, 0.5% NaCl) at 37° C. for 16 hours, and a single-stranded DNA was purified from the culture supernatant by precipitation with PEG #6000, extraction with phenol and precipitation with ethanol. The nucleotide sequence of the cDNA portion of the purified DNA was determined using α- $^{32}$p-dCTP (~800 Ci/mmole, Amersham) and the Sequenase Ver. 2.5 kit (U.B.C.). The thus-determined nucleotide sequence and the amino acid sequence deducible therefrom are shown in FIG. 4 and under SEQ. ID No. 3.

Example 9 Construction of a gene map of pTB1352

Figure 5:
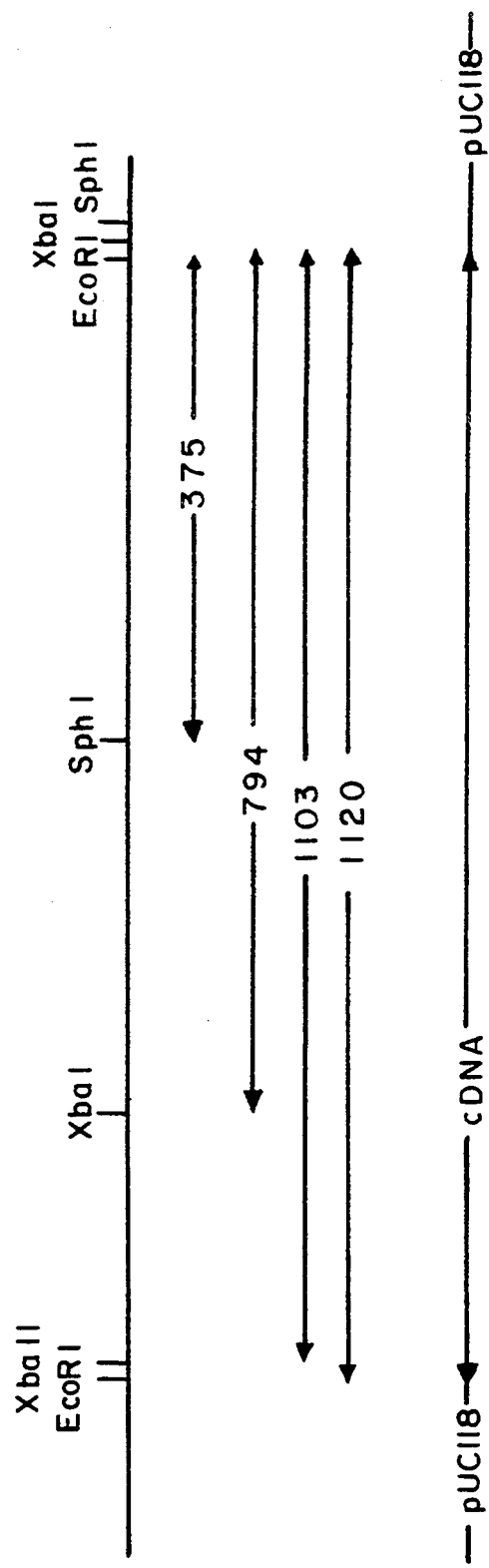
FIG. 5 shows a gene map of the plasmid pTB1352 constructed in Example 7.

The transformant obtained in Example 7 was cultured in 2×YT medium at 37° C. for 16 hours, and a double-stranded DNA was purified therefrom using the QIAGEN>plasmid<kit. The DNA obtained was digested with the restriction enzymes SacI, KpnI, SmaI, BamHI, XbaI, SalI, PstI, SphI and HindIII, and the digests were analyzed by 1% agarose gel electrophoresis. It was found that the DNA had two XbaI cleavage sites and one SphI cleavage site. Then double digestion was carried out with XbaI-EcoRI and with SphI-EcoRI to complete the gene map shown in FIG. 5.

Example 10 Construction of an expression plasmid for animal cells

The known plasmid pTB399 [Japanese Unexamined Publication No. 63282/1985, Example 1 (v)] was cleaved with the restriction enzyme EcoRI, then rendered blunt-ended using DNA polymerase (Klenow fragment), and joined with a 5'-terminally phosphorylated BqlII linker (CAGATCTG) by a known method. After cleavage of the product with BqlII, a 3.9 Kb DNA fragment was separated and purified by agarose gel electrophoresis. This DNA fragment was circularized by the T4 DNA ligase reaction to give a plasmid, pTB1308, containing the A-MuLV LTR region, splicing region and poly-A addition region. The plasmid pTB1308 was then cleaved with the restriction enzyme EcoRI. The cleavage product was mixed with an gene fragment encoding M (1.1 Kb) separately prepared by cleavage of the plasmid pTB1352 obtained in Example 7 with the restriction enzyme EcoRI and isolation by agarose gel electrophoresis, and a plasmid, pTB1308/M, was constructed by the T4 DNA ligase reaction.

Figure 6:
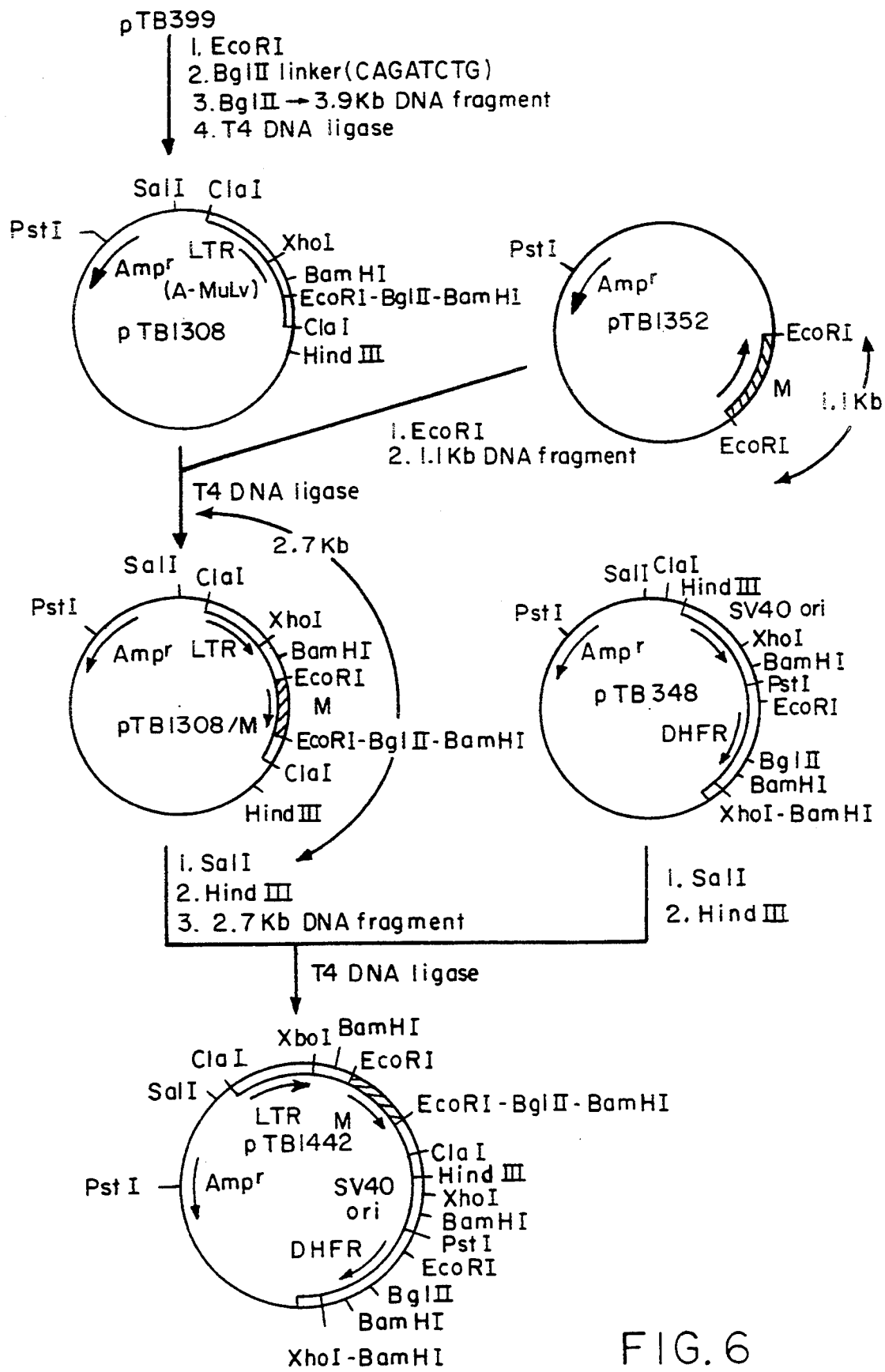
FIG. 6 shows a restriction enzyme map of the M expression plasmid pTB1442 constructed in Example 10.

Similarly, the known plasmid pTB348 [Japanese Publication No. 63282/1985, Example 1 (v)] was cleaved with the restriction enzymes SalI and HindIII, the cleavage product was mixed with a DNA fragment (2.7 Kb) separately prepared by cleavage of the plasmid pTB1308/M obtained as described above with the restriction enzymes SalI and HindIII followed by isolation by agarose gel electrophoresis and containing the gene encoding M, A-MuLV LTR region, splicing region and poly-A addition region, and an expression plasmid for M, pTB1442 (FIG. 6) was constructed by the T4 DNA ligase reaction. The thus-obtained plasmid pTB1442 was used to transfect *Escherichia coli* DH1 to give a transformant, *Escherichia coli* DH1/pTB1442.

Example 11 Expression of pTB1442 and production of a transformant i) CHO cells

Figure 7:
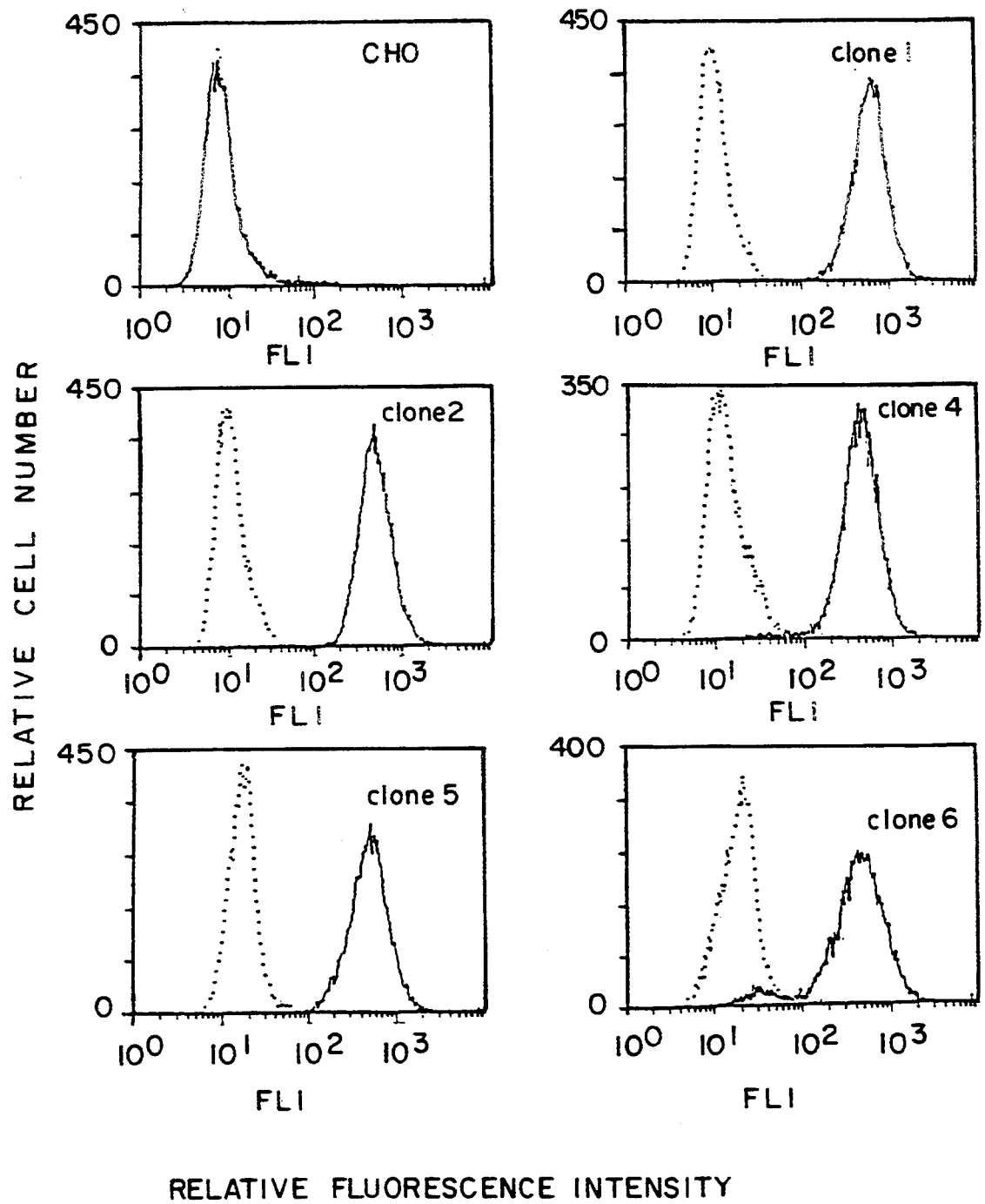
FIG. 7 shows the FACStar analysis patterns obtained in Example 11 for CHO(dhfr−) cells and M-expressing clones derived therefrom.

Hamster DHFR$^-$CHO cells (hereinafter referred to briefly as CHO cells) [Proc. Natl. Acad. Sci. USA, 77, 4216-4220 (1980)] were cultured in Falcon dishes (6 cm in diameter; Becton Dickinson, CA) using 5% FBS/Ham's F-12 medium. According to the method of Graham [Virology, 52, 456–467 (1973)], CHO cells were transfected with the pTB1442 (10 μg per dish). After 2 days, the medium was replaced with 10% dialyzed FBS/proline (35 μg/ml)/Dulbecco's modified MEM and, 2 weeks later, colonies that had become DHFR+ and had grown were obtained. The detection of expression of M was done according to the procedure described in Example 2. The results are shown in FIG. 7.

ii) MAC10 cells

For the transfection of MAC10 cells, the electroporation method [EMBO J., 1, 841 (1982)] was used. Thus, $5 \times 10^6$ MAC10 cells were transfected with a mixture of 20 μg of the plasmid pTB1442 and 2 μg of pRc/CMV (Invitrogen, CA), diluted to a concentration of $2.5 \times 10^5$ cells/ml with 10% FBS/RPMI1640 medium, and sowed in 100 μl portions into wells of a 96 well plate. 10% FBS/RPMI1640 medium containing 1 mg/ml of G418 (Sigma) was used as a selective medium. After about 2 to 3 weeks, 17 G418-resistant colonies were obtained.

Example 12 Assay of M by the dot blot method i) Solubilization of cells.

The cells obtained in Example 11 were cultured in a dish having a diameter of 10 cm, and washed with 2 ml of PBS and then with 1 ml of 0.1M Tris buffer (pH 8.1), and 0.5 ml of 0.1 M Tris buffer was added. The cells were collected into an Eppendorf 3810 tube using a cell scraper (Costar). The cells remaining in the dish were collected using a further 0.5 ml portion of 0.1 M Tris buffer. To the cells was added 50 μl of 1% CHAPS [3-[(3-cholamidopropyl)dimethylammonio]-1-propane-sulfonate; Boehringer Mannheim]/0.1M Tris, pH 8.1/10 mM EDTA/0.2 mM p-APMSF [(p-amidinophenyl)methanesulfonyl fluoride hydrochloride; Wako Pure Chemical Industrial Ltd.]/trasylol (2 units/ml), the mixture was kept at 0° C. for 30 minutes for solubilization and then centrifuged and the supernatant was used.

ii) Assay by the dot blot method.

A nitrocellulose membrane (Bio-Rad, Richmond, CA) was spotted with 1 μl of the extract obtained in above i) or a dilution thereof and, after air drying, immersed overnight in TBS (20 mM Tris/500 mM sodium chloride, pH 7.5) containing 2% FBS. The membrane was then reacted with 1% gelatin/TBS containing the monoclonal antibody M31-15 (1 μg/ml) at 37° C. for 1 hour, then washed twice with TBS containing 0.05% Tween 20 (TTBS) for 10 minutes and once with TBS, and reacted with 1% gelatin/TBS containing HRP-labeled anti mouse antibody (1,000-fold diluted) at 37° C. for 1 hour. The membrane was washed twice with TTBS for 10 minutes and once with TBS, and then immersed in a color developing solution [HRP color development reagent (Bio-Rad) 20 mg/methanol 6.6 ml/aqueous hydrogen peroxide 20 μl/TBS 33.4 ml] for 10 minutes for color development. The membrane was thoroughly washed with distilled water and then air-dried. The titer of a MAC10 cell extract was taken as 10 units (U)/ml. The same assay was performed to the extracts from several MAC10 cell clones resulting from expression of the plasmid pTB1442. The results are shown in Table 5. For the quantitative analysis of protein, the BCA protein assay reagent (PIERCE, Rockford, Illynois) was used.

TABLE 5

|  | M (U/ml) | Amount of protein (mg/ml) | U/mg |
| --- | --- | --- | --- |
| MAC10 | 10 | 10 | 1.0 |
| Clone 1 | 60 | 19 | 3.2 |
| Clone 4 | 20 | 19 | 1.1 |
| Clone 7 | 10 | 11 | 0.9 |
| Clone 9 | 40 | 17 | 2.4 |
| Clone 11 | 10 | 9.6 | 1.0 |

Example 13 Synthesis and purification of M fragment peptides

The synthesis of M fragment peptides was carried out on an automated peptide synthesizer (Applied Biosystems model 430A) using a modification of the method of solid phase peptide synthesis developed by Merrifield et al. [R.B. Merrifield, Advances in Enzymology, 32, 221–296 (1969)]. For protected peptide-resin synthesis, the protocol designated by Applied Biosystems was used. A protected amino acid-p-hydroxymethyl-phenylacetamidomethyl-resin (polystyrene-1% divinylbenzene) was used as the starting material and successively condensed with protected amino acids. For protecting the α-amino group of each amino acid in the condensation step, a tert-butyloxycarbonyl group (BOC) was used. The side chain functional groups were protected as follows: the hydroxy group of serine and threonine were protected as an O-benzyl ether; the hydroxy group of tyrosine was protected as a p-bromobenzyloxycarbonyl ester; the carboxy group of glutamic acid and aspartic acid were protected as a benzyl ester; the imidazole nitrogen of histidine were protected by benzyloxymethyl; the side chain amino group of lysine were protected by 2-chlorobenzyloxycarbonyl; the guanidine functional group of arginine were protected by p-toluenesulfonyl; and the indole imine of tryptophan were protected by formyl. All amino acids used herein were purchased either from Applied Biosystems Japan or from Bachem Chemicals.

After condensation of all the amino acid on the resin, the protected peptide-resin was taken out of the synthesizer and dried. The peptide-resin (1 g) was reacted with anhydrous hydrogen fluoride (8 ml) containing p-cresol (1 ml), 1,2-ethanedithiol (1 ml) and 2-mercaptopyridine (100 mg) at 0° C. for 2 hours. After completion of the reaction, the hydrogen fluoride was distilled off, and the residue was washed with diethyl ether for removing most of the remaining reagents. The peptide was extracted with trifluoroacetic acid (10 ml) and the resin was removed by filtration. The filtrate was concentrated and ether was added to the concentrate to give a precipitate, which was collected by centrifugation and washed three times with ether. The thus-obtained powder sample was further purified by reversed-phase high-performance liquid chromatography [column YMC A-303 ODS (4.6×250 mm); elution solvent A, 0.1% trifluoroacetic acid-99.9% water; elution solvent B, 0.1% trifluoroacetic acid-99.9% acetonitrile; elution concentration gradient program, minute 0 (80% A+20% B)-minute 30 (50% A+50% B) (another elution program may be used if necessary); elution speed, 1 ml/min.; detection wavelength 230 or 280 μm]. Peak fractions containing the pure desired product were collected and passed through a column of Bio-Rad AGI×8 (acetic acid form, 1.8×5 cm), the effluent and washings were combined, the acetonitrile was distilled off, and the residue was lyophilized.

The results of amino acid analysis of the peptides obtained in the above manner are shown in Table 6. The amino acid sequences of these peptides as well as the retention times thereof in reversed-phase high-performance liquid chromatography are also shown below.

TABLE 6

| | Peptide Found (theoretical) | | | |
| --- | --- | --- | --- | --- |
| | 1 | 2 | 3 | 4 |
| Asp | 4.0(4) | 2.0(2) | 5.1(5) | 5.0(5) |
| Thr | 2.6(3) | 0.9(1) | 1.9(2) | 2.5(3) |
| Ser |  | 0.9(1) | 1.9(2) | 3.3(4) |
| Glu | 7.1(7) | 4.2(4) | 2.1(2) | 4.0(4) |
| Pro |  |  | 2.1(2) |  |
| Gly |  | 3.0(3) |  | 1.1(1) |
| Ala |  | 3.0(3) | 1.1(1) |  |
| ½Cys |  | 2.8(3) | 1.8(2) |  |
| Val | 1.6(2) | 1.0(1) | 2.9(3) | 1.0(1) |
| Ile | 0.7(1) | 2.8(3) | 1.9(2) | 0.9(1) |
| Leu | 2.0(2) | 3.0(3) | 1.0(1) |  |
| Tyr | 1.9(2) | 1.0(1) |  | 2.0(2) |

TABLE 6-continued

|     | Peptide Found (theoretical) | | | |
| --- | --- | --- | --- | --- |
|     | 1 | 2 | 3 | 4 |
| Phe | 1.0(1) | 1.0(1) | 2.0(2) | 3.0(3) |
| Lys | 5.7(6) | 1.0(1) | 4.9(5) | 0.9(1) |
| His |  | 0.9(1) |  |  |
| Arg | 0.9(1) | 1.0(1) | 0.9(1) |  |

Each peptide sample was subjected to amino acid analysis following 24 hours of hydrolysis with 6N hydrochloric acid in a sealed tube at 110° C. Cys was quantitated as cystenic acid following performic acid oxidation.

Peptide 1: Lys—Asp—Glu—Val—Ile—Lys—Glu—Val—Gln—
Glu—Phe—Tyr—Lys—Asp—Thr—Tyr—Asn—
Lys—Leu—Lys—Thr—Lys—Asp—Glu—Pro—
Gln—Arg—Glu—Thr—Leu Retention time: 19.0 min. [minute 0 (74% A+26% B)-minute 30 (59% A+41% B), 0.7 ml/min.]
[SEQ ID NO. 4 comprising amino acid residues Nos. 113-142 of SEQ. ID NO. 1]

Peptide 2: Gln—Arg—Glu—Thr—Leu—Lys—Ala—Ile—His—
Tyr—Ala—Leu—Asn—Cys—Cys—Gly—Leu—
Ala—Gly—Gly—Val—Glu—Gln—Phe—Ile—Ser—
Asp—Ile—Cys Retention time: 28.2 min.
[SEQ ID NO. 5 comprising amino acid residues Nos. 138-166 of Seq. ID NO. 1]

Peptide 3: Ser—Asp—Ile—Cys—Pro—Lys—Lys—Asp—Val—
Leu—Glu—Thr—Phe—Thr—Val—Lys—Ser—Cys—
Pro—Asp—Ala—Ile—Lys—Glu—Val—Phe—Asp—
Asn—Lys—

Retention time: 16.0 min.
[SEQ ID NO. 6 comprising amino acid residues Nos. 163-191 of SEQ. ID NO. 1]

Peptide 4: Arg—Phe—Asp—Ser—Gln—Thr—Lys—Ser—Ile—
Phe—Glu—Gln—Glu—Thr—Asn—Asn—Asn—
Asn—Ser—Ser—Phe—Tyr—Thr—Gly—Val—Tyr Retention time: 24.3 min. [0.7 ml/min.] [SEQ ID NO. 7 comprising amino acid residues Nos. 35-60 of SEQ. ID NO. 1

Peptides 1 and 3 were each dissolved in PBS and peptide 2 was dissolved in 5% acetic acid, each to a final concentration of 1 mg/ml. The solutions were diluted with RPMI1640 medium and the dilutions were used in the following experiments.

Figure 8:
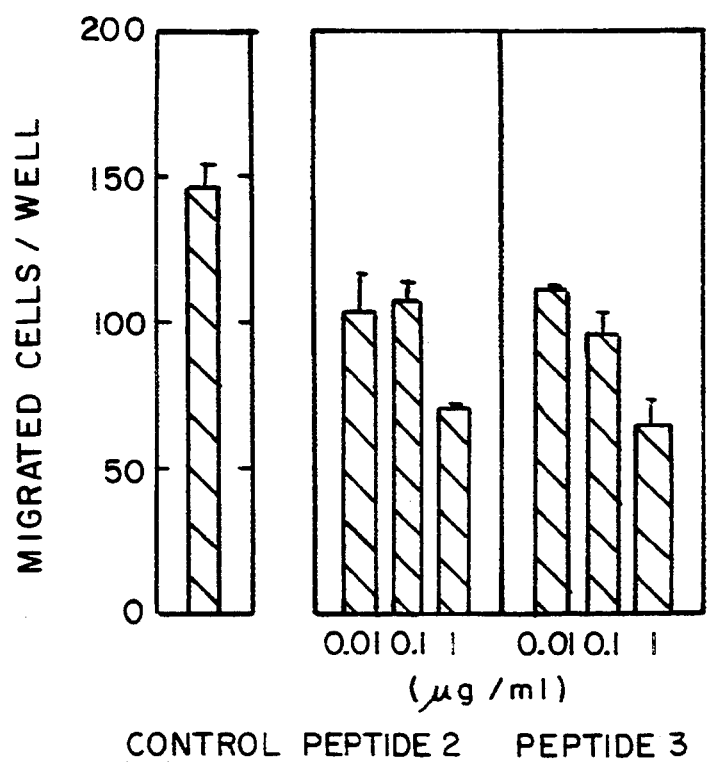
FIG. 8 graphically shows the results of Experimental Example 4 concerning the suppression of the motility of MAC10 cells by some M fragment peptides.

Experimental Example 4 Suppression of the cancer cell motility by M fragment peptides MAC10 cells were detached from the culture flask using PBS containing 0.01% EDTA and 0.125% trypsin, rinsed with 10% FBS/RPMI1640 and then twice with RPMI1640 medium, and suspended to a concentration of 5×10 cells/ml (FBS concentration 0.05%). Dilutions (10-1,000 ng/ml) of the peptides 2 and 3 obtained in Example 13 were respectively added in 0.6 ml portions to lower chambers of a Transwell plate (Costar, Cambridge, MA), followed by addition of 0.1 ml of the MAC 10 cell suspension to each upper chamber. Incubation was performed at 37° C. for 16 hours. The cells that had passed through the membrane and migrated into the lower chamber were counted under a phase contrast microscope. As shown in FIG. 8, peptides 2 and 3 showed an inhibitory activity in a concentration-dependent manner.

Figure 9:
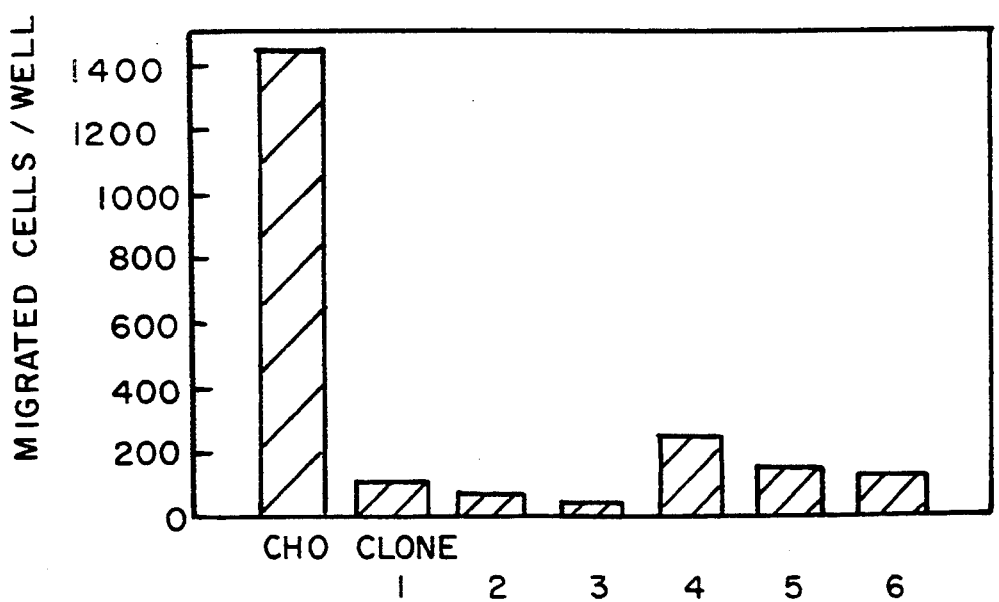
FIG. 9 shows the motilities of CHO(dhfr−) cells and some M-expressing clones derived therefrom as measured in Experimental Example 5.

Experimental Example 5 Suppression of the motility as a result of expression of M i) CHO cell clones The CHO cell clones obtained in Example 11 were tested by the method described in Experimental Example 4. The motility values thus measured are shown in FIG. 9. With the clones in which M had been expressed, marked decreases in motility were observed as compared with the parent strain (CHO).

ii) MAC10 cell clones

Some of the MAC10 clones obtained in Example 11 were tested by the method described in Experimental Example 4. The motility data obtained are shown in Table 7 together with the levels of expression of M as obtained in Example 12. Decreases in motility were observed due to excessive expression of M.

TABLE 7

|  | Number of migrant cells | | M |
| --- | --- | --- | --- |
|  | Experiment 1 | Experiment 2 | (U/mg) |
| MAC10 | 208 ± 23 (100%) | 235 ± 33 (100%) | 1.0 |
| Clone 1 | 83 ± 10 (40%) | 102 ± 23 (42%) | 3.2 |
| Clone 4 | 205 ± 10 (99%) | 188 ± 27 (80%) | 1.1 |
| Clone 9 | 73 ± 23 (35%) | 150 ± 18 (64%) | 2.4 |

N = 3 ± SD

What is claimed is:

1. A polypeptide having the amino acid sequence of amino acid residue numbers 138-191 of SEQ ID NO:1 or a portion thereof, wherein said polypeptide is capable of suppressing cell motility in vitro activity.

2. The polypeptide according to claim 1, which has the amino acid sequence of SEQ ID NO:5 or a portion thereof.

3. The polypeptide according to claim 1, which has the amino acid sequence of SEQ ID NO:6 or a portion thereof.

* * * * *